US011209441B2

(12) United States Patent
Farsaci

(10) Patent No.: US 11,209,441 B2
(45) Date of Patent: Dec. 28, 2021

(54) CYTOKINE PROFILING ANALYSIS

(71) Applicant: Bristol-Myers Squibb Company, Princeton, NJ (US)

(72) Inventor: Benedetto Farsaci, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 305 days.

(21) Appl. No.: 16/091,441

(22) PCT Filed: Apr. 5, 2017

(86) PCT No.: PCT/US2017/026212
§ 371 (c)(1),
(2) Date: Oct. 4, 2018

(87) PCT Pub. No.: WO2017/176925
PCT Pub. Date: Oct. 12, 2017

(65) Prior Publication Data
US 2019/0154701 A1    May 23, 2019

Related U.S. Application Data

(60) Provisional application No. 62/318,701, filed on Apr. 5, 2016.

(51) Int. Cl.
*G01N 33/68* (2006.01)
*G01N 33/574* (2006.01)
*C07K 16/28* (2006.01)

(52) U.S. Cl.
CPC ..... *G01N 33/6863* (2013.01); *C07K 16/2803* (2013.01); *G01N 33/57423* (2013.01); *G01N 33/57484* (2013.01); *G01N 2333/52* (2013.01); *G01N 2800/52* (2013.01)

(58) Field of Classification Search
None
See application file for complete search history.

(56) References Cited

U.S. PATENT DOCUMENTS

| 5,977,318 A | 11/1999 | Linsley et al. |
| 6,051,227 A | 4/2000 | Allison et al. |
| 6,682,736 B1 | 1/2004 | Hanson et al. |
| 6,808,710 B1 | 10/2004 | Wood et al. |
| 6,984,720 B1 | 1/2006 | Korman et al. |
| 7,034,121 B2 | 4/2006 | Carreno et al. |
| 7,488,802 B2 | 2/2009 | Collins et al. |
| 7,595,048 B2 | 9/2009 | Honjo et al. |
| 7,605,238 B2 | 10/2009 | Korman et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,354,509 B2 | 1/2013 | Carven et al. |
| 8,609,089 B2 | 12/2013 | Langermann et al. |
| 8,728,474 B2 | 5/2014 | Honjo et al. |
| 8,779,105 B2 | 7/2014 | Korman et al. |
| 8,779,108 B2 | 7/2014 | Queva et al. |
| 8,900,587 B2 | 12/2014 | Carven et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,212,224 B2 | 12/2015 | Cogswell et al. |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 9,492,539 B2 | 11/2016 | Korman et al. |
| 9,492,540 B2 | 11/2016 | Korman et al. |
| 9,856,320 B2 | 1/2018 | Cogswell et al. |
| 10,072,082 B2 | 9/2018 | Cogswell et al. |
| 2012/0263677 A1 | 10/2012 | Eagle et al. |
| 2013/0017199 A1 | 1/2013 | Langermann |
| 2013/0309250 A1 | 11/2013 | Cogswell et al. |
| 2014/0341917 A1 | 11/2014 | Nastri et al. |
| 2014/0356353 A1 | 12/2014 | Queva et al. |
| 2015/0079109 A1 | 3/2015 | Li et al. |
| 2015/0125463 A1 | 5/2015 | Cogswell et al. |
| 2016/0090417 A1 | 3/2016 | Cogswell et al. |
| 2017/0051060 A1 | 2/2017 | Honjo et al. |
| 2017/0088615 A1 | 3/2017 | Korman et al. |
| 2018/0273624 A1 | 9/2018 | Cogswell et al. |

FOREIGN PATENT DOCUMENTS

| WO | WO-2007113648 A2 | 10/2007 |
| WO | WO-2012122444 A1 | 9/2012 |
| WO | WO-2012145493 A1 | 10/2012 |
| WO | WO-2013173223 A1 | 11/2013 |
| WO | WO-2015134605 A1 | 9/2015 |
| WO | WO-2015176033 A1 | 11/2015 |
| WO | WO-2016034718 A1 | 3/2016 |
| WO | WO-2016100561 A2 | 6/2016 |
| WO | WO-2017176925 A1 | 10/2017 |

OTHER PUBLICATIONS

Chen et al. (British Journal of Cancer, 112: 1088-1097, 2015).*
Carbognin et al. (PLOS ONE, DOI:10.1371/journal.pone.0130142: 1-16, 2015).*
Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (Jul. 2010).
Choueiri, T.K., et al., "Immunomodulatory activity of nivolumab in previously treated and untreated metastatic renal cell carcinoma (mRCC): Biomarker-based results from a randomized clinical trial.", May 31, 2014 (May 31, 2014). XP055376753, Retrieved from the Internet: URL:http://meetinglibrary.asco.org/record/94600/abstract [retrieved on May 29, 2017].

(Continued)

*Primary Examiner* — Nelson B Moseley, II
(74) *Attorney, Agent, or Firm* — Sterne, Kessler, Goldstein & Fox P.L.L.C.

(57) ABSTRACT

This invention relates to methods for predicting a prognosis of a patient with cancer in need of an anti-cancer treatment comprising measuring a cytokine score from a sample obtained from the patient. In some embodiments, the subject is administered an anti-cancer treatment, e.g., an anti-PD-1 antibody, following the cytokine score measurement. In some embodiments, the cancer is lung cancer.

10 Claims, 12 Drawing Sheets

(56) References Cited

OTHER PUBLICATIONS

Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).
Drake, "Safety, Durable Clinical Benefit, and Remission Resulting from Nivolumanb (Anti-PD-1; BMS-936558; ONO-4538) in a Phase 1 Trial In Patients With Previously Treated Metastatic Renal Cell Carcinoma (mRCC); Long-Term Patient Follow-Up, Abstracts of the 12th International Kidney Cancer Symposium. Oct. 25-26, 2013. Chicago, Illinois, USA," BJU International 112 (Suppl 3):1-17, Blackwell Science, England (Nov. 2013).
Dulos, J., et al., "PD-1 Blockade Augments Th1 and Th17 and Suppresses Th2 Responses in Peripheral Blood From Patients With Prostate and Advanced Melanoma Cancer," Journal of Immunotherapy 35(2):169-178, (Feb.-Mar. 2012).
GenBank, "Human hPD-1 (hPD-1) mRNA, complete cds," Accession No. U64863.1, accessed on https://www.ncbi.nlm.nih.gov/nuccore/U64863, Oct. 12, 2005.
GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, accessed on https://www.ncbi.nlm.nih.gov/protein/Q9NZQ7, Nov. 2, 2016.
Goldinger, S.M., et al.,, "Cytotoxic Cutaneous Adverse Drug Reactions during Anti-PD-1 Therapy," Clinical Cancer Research 22(16):4023-4029, The Association, United States (Aug. 2016).
Hamid, O. and Carvajal, R.D., "Anti-programmed Death-1 and Anti-programmed Death-ligand 1 Antibodies in Cancer Therapy," Expert Opinion on Biological Therapy 13(6):847-861, Taylor & Francis, England (Jun. 2013).
Hamid, O., et al., "Safety and Tumor Responses with Lambrolizumab (Anti-Pd-1) in Melanoma," The New England Journal of Medicine 369(2):134-144, Massachusetts Medical Society, United States of America (Jul. 2013).
Hanna, N., et al., "Randomized Phase III Trial of Pemetrexed Versus Docetaxel in Patients with Non-small-cell Lung Cancer Previously Treated with Chemotherapy," Journal of Clinical Oncology 22(9):1589-1597, American Society of Clinical Oncology, United States(May 2004).
Hodi, F.S., et al., "Improved Survival with Ipilimumab in Patients with Metastatic Melanoma," The New England Journal of Medicine 363(8):711-723, Massachusetts Medical Society, United States (Aug. 2010).
Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).
Lena, H., et al., "Nivolumab In Patients With Advanced Refractory Squamous (SQ) NSCLC: 2-Year Follow-Up From Checkmate 063 and Exploratory Cytokine Profiling Analyses", http://oncologypro.esmo.org/Meeting-Resources/ELCC-2016/Nivolumab-in-patients-pts-with-advanced-refractory-squamous-SQ-non-small-cell-lung-cancer-NSCLC-2-year-follow-up-from-CheckMate-063-and-exploratory-cytokine-profiling-analyses, Apr. 15, 2016 (Apr. 15, 2016). XP055376011, European Lung Cancer Conference 2016 Retrieved from the Internet: URL:https://cslide.ctimeetingtech.com/elcc2016/public/download_Uploaded_media/pdf/259 [Retrieved on May 24, 2017].
Lena, H., et al. "Nivolumab in patients (pts) with advanced refractory squamous (SQ) non-small cell lung cancer (NSCLC): 2-year follow-up from CheckMate 063 and exploratory cytokine profiling analyses", Abstracts. ELCC 2016—Advanced NSCLC. Apr. 1, 2016 (Apr. 1, 2016). XP055376015. Retrieved from the Internet: URL:http://www.jto.org/article/S1556-0864(16)30247-7/pdf [retrieved on May 24, 2017].

McCabe, K.E. and Wu, A.M., "Positive Progress in ImmunoPET—not Just a Coincidence," Cancer Biotherapy & Radiopharmaceuticals 25(3):253-261, Mary Ann Liebert, Inc, United States (Jun. 2010).
McDermott, D.F., and Atkins, M.B., "PD-1 as a Potential Target in Cancer Therapy," Cancer Medicine 2(5):662-673, John Wiley & Sons Ltd., United States (Oct. 2013).
National Cancer Institute, Colorectal Cancer, available at: http://www.cancer.gov/types/colorectal, last visited Dec. 9, 2015.
National Cancer Institute, Head and Neck Cancers, available at https://www.cancer.gov/types/head-and-neck/head-neck-fact-sheet, last visited Dec. 9, 2015.
National Cancer Institute, Ovarian Epithelial, Fallopian Tube, and Primary Peritoneal Cancer Treatment (PDQ®), available at https://www.cancer.gov/types/ovarian/patient/ovarian-epithelial-treatment-pdq, last visited Dec. 9, 2015.
National Cancer Institute, Skin Cancer (Including Melanoma), available at http://www.cancer.gov/types/skin, last visited Dec. 9, 2015.
NCCN Guidelines® (2014), available at http://www.nccn.org/professionals/physician_gls/f_guidelines.asp, last accessed May 14, 2014.
NCCN Guidelines, Version 3.2014—Non-Small Cell Lung Cancer, available at: http://www.nccn.org/professionals/physician_gls_pdf/nscl.pdf, last accessed May 14, 2014.
NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.
NCI Drug Dictionary, anti-PD-1 monoclonal antibody MEDI0680, accessed on Dec. 1, 2016, retrieved from the Internet URL: https://www.cancer.gov/publications/dictionaries/cancer-drug?cdrid=756047.
NCI Drug Dictionary, pembrolizumab, accessed on Dec. 1, 2016, retrieved from the Internet URL: https://www.cancer.gov/drugdictionary?cancer-drug?cdrid=695789, 3 pages.
Ock, C.Y., et al., "Signature of Cytokines and Angiogenic Factors (CAFs) Defines a Clinically Distinct Subgroup of Gastric Cancer," Gastric Cancer 20(1):164-174, Springer-Verlag Tokyo, Japan (Jan. 2017).
Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, England (Apr. 2010).
Pawlik, T.M., et al., "Colorectal Carcinogenesis: MSI-H Versus MSI-L," Disease Markers 20(4-5):199-206, Hindawi Pub. Corp, United States (2004).
Powles, T., et al., "MPDL3280A (anti-PD-L1) Treatment Leads to Clinical Activity in Metastatic Bladder Cancer," Nature 515(7528):558-562, Nature Publishing Group, England (Nov. 2014).
Siegel, R., et al., "Cancer Statistics, 2014," CA: A Cancer Journal for Clinicians 64(1):9-29, Wiley, United States (Jan. 2014).
Sjoblom, T., et al., "The Consensus Coding Sequences of Human Breast and Colorectal Cancers," Science 314(5797):268-274, American Association for the Advancement of Science, United States (Oct. 2006).
International Search Report and Written Opinion for Application No. PCT/US2017/026212, dated Aug. 3, 2017, 17 pages.
Taube, J.M., et al., "Colocalization of Inflammatory Response with B7-H1 Expression in Human Melanocytic Lesions Supports an Adaptive Resistance Mechanism of Immune Escape," Science Translational Medicine 4(127):127ra37, American Association for the Advancement of Science, United States (Mar. 2012).
Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).
Topalian, S.L., et al., "Targeting the PD-1/B7-H1 (PD-L1) Pathway to Activate Anti-tumor Immunity," Current Opinion in Immunology 24(2):207-212, Elsevier, England (Apr. 2012).
Topalian, S.L., et al., "Survival, Durable Tumor Remission, and Long-term Safety in Patients with Advanced Melanoma Receiving Nivolumab," Journal of Clinical Oncology 32(10):1020-1030, American Society of Clinical Oncology, United States (Apr. 2014).

(56) References Cited

OTHER PUBLICATIONS

United States Adopted Name (USAN) Drug Finder, Pembrolizumab: Statement on a nonproprietary name adopted by the USAN Council (ZZ-165), published Nov. 27, 2013, accessed at htttps://searchusan.ama-amaassn.org/usan/documentDownload?uri=%2Funstructured%2Fbina[Y%2Fusan%2Fpembrolizab.pdf, accessed on Dec. 8, 2016, 2 pages.

Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).

* cited by examiner

FIG. 2A
Cytokines associated with OS identified via stepwise variable selection in Cox model using AIC:
| IL-8 | VWF | MICA | CRP | IL-6 |
|---|---|---|---|---|
| FRTN | MIG | IP-10 | IL-18 | MIP1B |
| ICAM1 | IL-1RA | MMP3 | VDBP | |
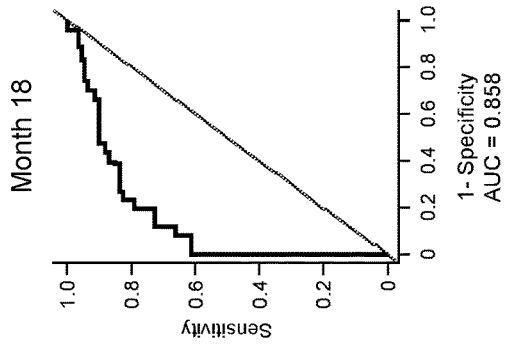
FIG. 2F — Month 18, AUC = 0.858
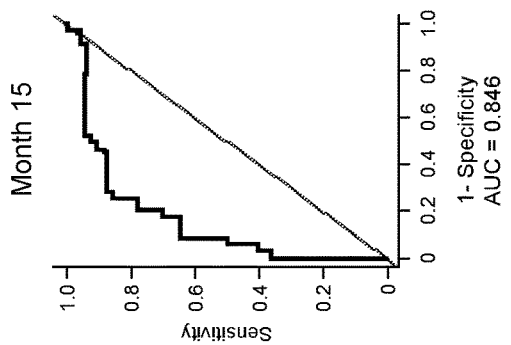
FIG. 2E — Month 15, AUC = 0.846
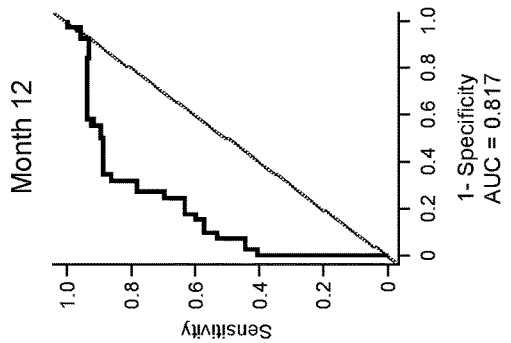
FIG. 2D — Month 12, AUC = 0.817
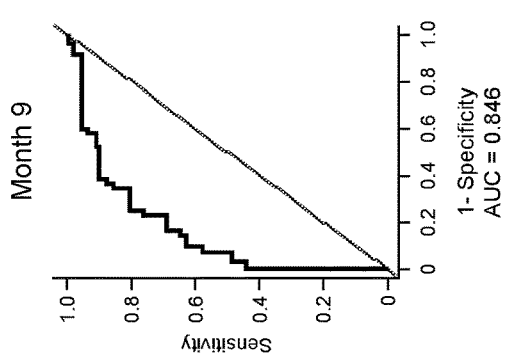
FIG. 2C — Month 9, AUC = 0.846
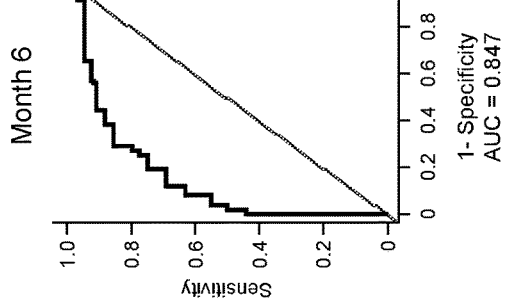
FIG. 2B — Month 6, AUC = 0.847

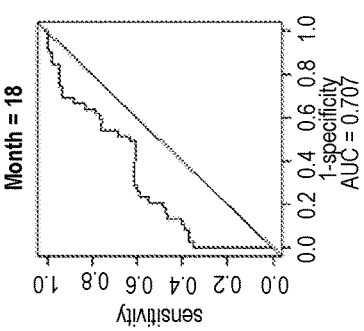 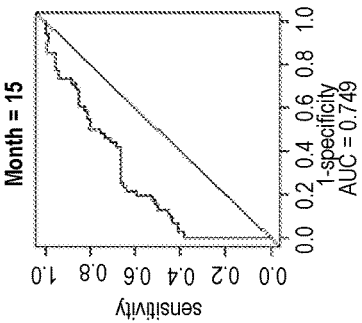 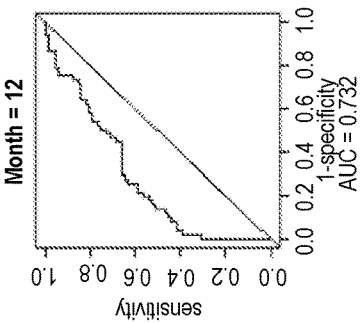 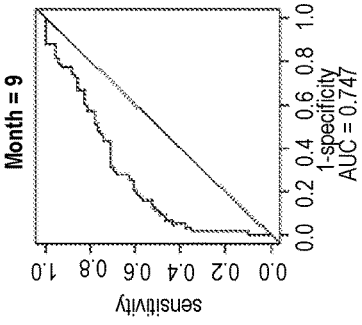 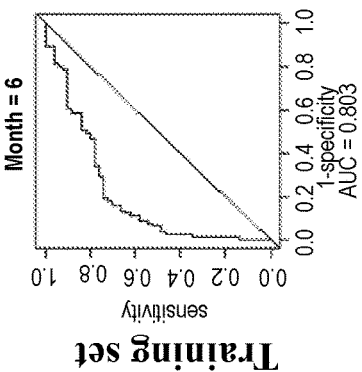 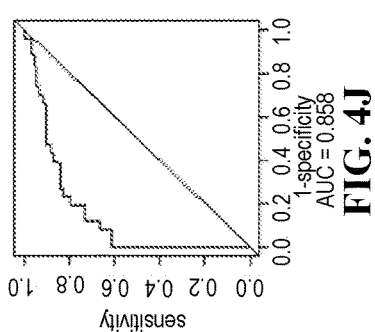 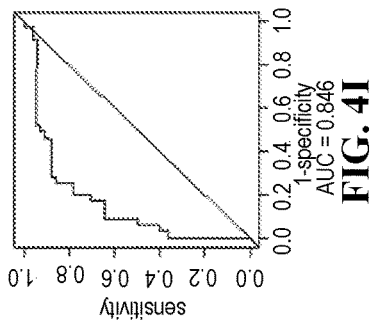 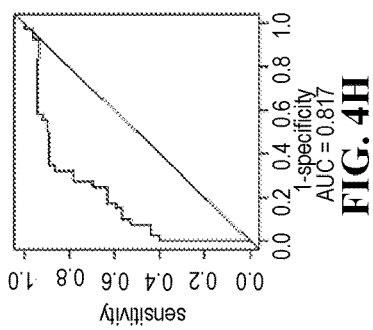 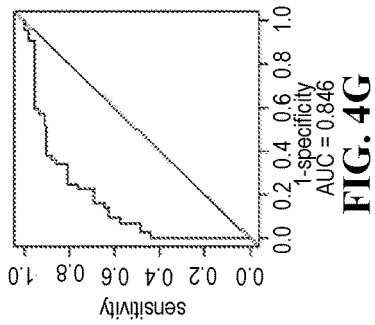 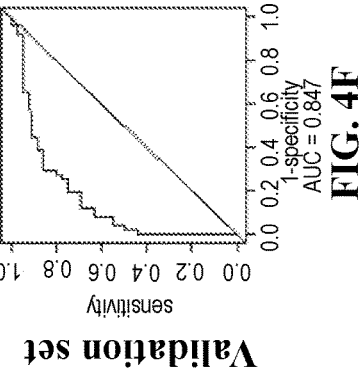
FIG. 4A Month = 6; FIG. 4B Month = 9; FIG. 4C Month = 12; FIG. 4D Month = 15; FIG. 4E Month = 18; FIG. 4F; FIG. 4G; FIG. 4H; FIG. 4I; FIG. 4J High cytoscore:
Δ OS: +6.5 months if treated with Nivo Low cytoscore:
Δ OS: +0.4 months if treated with Nivo

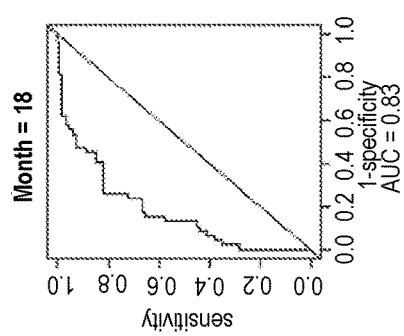
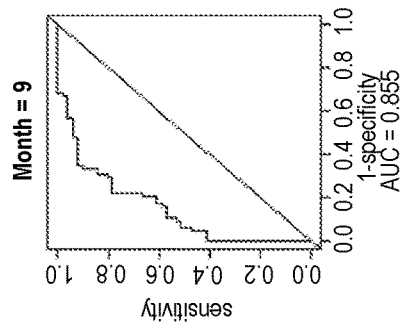
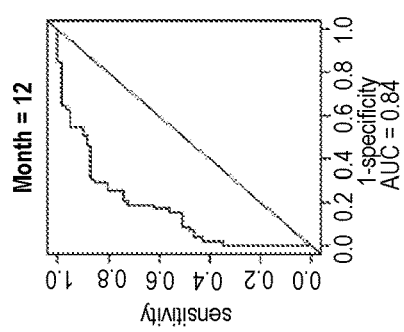
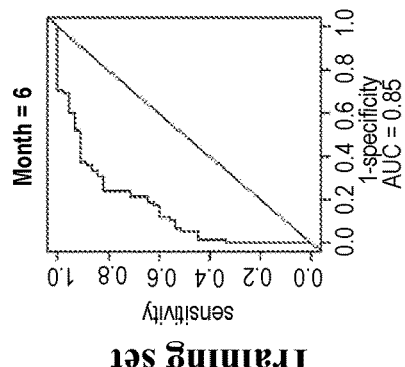
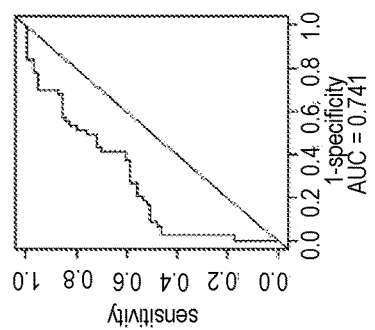
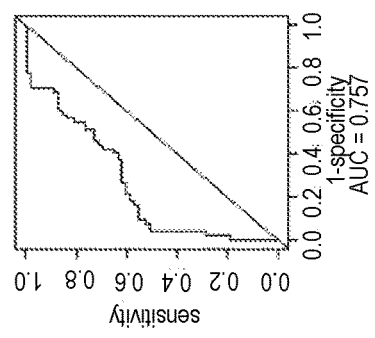
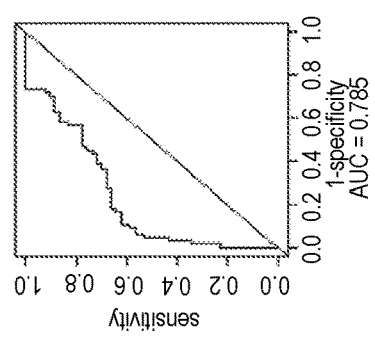
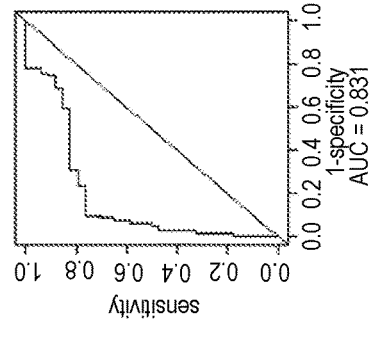
FIG. 10A  FIG. 10B  FIG. 10C  FIG. 10D  FIG. 10E
FIG. 10F  FIG. 10G  FIG. 10H  FIG. 10I  FIG. 10J Nivolumab:
Δ OS: +12 months if high cytoscore Docetaxel:
Δ OS: +3 months if high cytoscore High cytoscore:
Δ OS: +6.4 months if treated with Nivo Low cytoscore:
Δ OS: NS

CYTOKINE PROFILING ANALYSIS

FIELD OF THE INVENTION

This invention relates to methods for predicting the prognosis of a patient with cancer in need of an anti-cancer treatment comprising measuring cytokine concentrations and determining a cytokine score from a sample obtained from the patient. In some embodiments, the subject is administered an anti-cancer treatment, e.g., an anti-PD-1 or anti-PD-L1 antibody, following the cytokine score measurement. In some embodiments, the cancer is lung cancer.

BACKGROUND OF THE INVENTION

Human cancers harbor numerous genetic and epigenetic alterations, generating neoantigens potentially recognizable by the immune system (Sjoblom et al., (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of an antibody, ipilimumab (YERVOY®), that binds to and inhibits CTLA-4 for the treatment of patients with advanced melanoma (Hodi et al., (2010)*N Engl J Med* 363:711-23) and the development of antibodies, such as nivolumab and pembrolizumab (formerly lambrolizumab; USAN Council Statement, 2013), that bind specifically to the Programmed Death-1 (PD-1) receptor and block the inhibitory PD-1/PD-1 ligand pathway (Topalian et al., *N Engl J Med* 366:2443-54 (2012a); Topalian et al., *Curr Opin Immunol* 24:207-12 (2012b); Topalian et al., *J Clin Oncol* 32(10):1020-30 (2014); Hamid et al., *N Engl J Med* 369:134-144 (2013); Hamid and Carvajal, *Expert Opin Biol Ther* 13(6):847-61 (2013); and McDermott and Atkins, *Cancer Med* 2(5):662-73 (2013)).

Anti-cancer agents often vary in their effectiveness based on the unique patient characteristics. There is a need for designing targeted therapeutic strategies that can predict which patients will respond to anti-cancer drugs and, thus, improve the clinical outcome for patients diagnosed with cancer.

SUMMARY OF THE INVENTION

The present invention relates to a method of predicting a prognosis of a patient in need of an anti-cancer treatment comprising measuring a cytokine score from a sample obtained from the patient. The cytokine score is the sum of a point designated to the level of at least one cytokine in the sample. The point is X if the sample has a high concentration of a cytokine that is positively associated with overall survival of the patient during the anti-cancer treatment or a low concentration of a cytokine that is negatively associated with overall survival of the patient during the anti-cancer treatment. The point is Z if the sample has a low concentration of a cytokine that is positively associated with the overall survival of the patient during the anti-cancer treatment or a high concentration of a cytokine that is negatively associated with the overall survival of the patient during the anti-cancer treatment. Optionally, the point is Y if the sample has a medium concentration of a cytokine that is either negatively or positively associated with overall survival of the patient during the anti-cancer treatment.

In certain embodiments, the method further comprises administering to the patient an anti-cancer treatment, wherein the cytokine score is higher than the average cytokine score.

In one embodiment, the cytokine score is at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, at least about 95%, at least about 99%, or 100% higher than the average cytokine score.

In one embodiment, X is any value, Z is a value that is lower than X, and, optionally, Y is a value that is between X and Z. In one embodiment, Z is 0, Y is 1, and X is 2.

In certain embodiments, the average cytokine score is any integer between 1 and 100, between 1 and 50, between 1 and 40, between 1 and 25, between 1 and 20, between 1 and 15, between 5 and 50, between 5 and 40, between 5 and 30, between 5 and 25, between 5 and 20, between 10 and 50, between 10 and 40, between 10 and 30, between 10 and 25, between 10 and 20, between 15 and 50, between 15 and 40, between 15 and 30, between 15 and 25, or between 15 and 20. In one embodiment, the average cytokine score is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, about 50, about 60, about 70, about 80, about 90, or about 100.

In certain embodiments, the at least one cytokine comprises two cytokines, three cytokines, four cytokines, five cytokines, six cytokines, seven cytokines, eight cytokines, nine cytokines, ten cytokines, cytokines, 12 cytokines, 13 cytokines, 14 cytokines, 15 cytokines 16 cytokines, 17 cytokines, 18 cytokines, 19 cytokines, or at least 20 cytokines.

In embodiments, the patient has lung cancer. In further embodiments, the lung cancer is non-small cell lung cancer. In other embodiments, the non-small cell lung cancer is squamous non-small cell lung cancer. In still further embodiments, the non-small cell lung cancer is non-squamous non-small cell lung cancer.

In an embodiment, the at least one cytokine is selected from the group consisting of monokine induced by gamma interferon (MIG), interleukin-1 receptor antagonist (M-IRA), matrix metalloproteinase-3 (MMP-3), interleukin-8 ferritin (FRTN), intracellular adhesion molecule (ICAM), von Willebrand factor (VWF), majorhistocompatibility-complex class I-related chain A (MICA), interferon gamma-induced protein 10 (IP-10), C-reactive protein (CRP), interleukin-18 (IL-18), vitamin D binding protein (VDBP), interleukin-6 microphage inflammatory protein-1β (MIP1B), and any combination thereof. In another embodiment, the at least one cytokine is selected from the group consisting of ferritin (FRTN), matrix metalloproteinase-3 (MMP-3), interleukin-8 (IL-8), monocyte chemoattractant protein 2 (MCP2), extracellular newly identified receptor for advanced glycation end-products binding protein (EN-RAGE), interleukin-2 receptor antagonist (IL-2RA), interleukin-18 (IL-18), von Willebrand factor (VWF), beta-2- microglobulin (B2M), regulated on activation, normal T cell expressed and secreted (RANTES), majorhistocompatibility-complex class I-related chain A (MICA), tumor necrosis receptor factor 2 (TNFR2), vitamin D binding protein (VDBP), and any combination thereof. In one embodiment, the positively associated cytokines are selected from the group consisting of MIG, IL-1RA, MMP-3, and any combination thereof. In an embodiment, the negatively associated cytokines are selected from the group consisting of IL-8, FRTN, ICAM, VWF, MICA, IP-10, CRP, IL-18, VDBP, IL-6, MIP1B, and any combination thereof. In a further embodiment, the positively associated cytokines are B2M, VDBP, or both. In embodiments, the negatively associated cytokines are selected from the group consisting of FRTN, MMP-3, IL-8, MCP2, ENRAGE, IL-2RA, IL-18, VWF, RANTES, MICA, TNFR2, and any combination thereof.

In certain embodiments, the anti-cancer treatment is an effective amount of an anti-PD-1 antibody or antigen-binding portion thereof ("anti-PD-1 antibody") or an effective amount of an anti-PD-L1 antibody or antigen-binding portion thereof ("anti-PD-L1 antibody"). In one embodiment, the anti-PD-1 antibody cross-competes with a reference antibody, which is nivolumab, for binding to human PD-1. In an embodiment, the anti-PD-1 antibody comprises a heavy chain constant region that is of a human IgG1, IgG2, IgG3, or IgG4 isotype. In other embodiments, the anti-PD-1 antibody is a chimeric, humanized, or human monoclonal anti-PD-1 antibody or an antigen-binding portion thereof. In further embodiments, the anti-PD-1 antibody is nivolumab. In other embodiments, the anti-PD-1 antibody is pembrolizumab.

In one embodiment, the anti-PD-L1 antibody cross-competes with a reference antibody selected from BMS-936559, MPDL3280A, MEDI4736, and MSB0010718C for binding to human PD-L1. In an embodiment, the anti-PD-L1 antibody is selected from BMS-936559, MPDL3280A, MEDI4736, and MSB0010718C.

EMBODIMENTS

E1. A method of predicting a prognosis of a patient in need of an anti-cancer treatment comprising measuring a cytokine score from a sample obtained from the patient, wherein the cytokine score is the sum of a point designated to the level of at least one cytokine in the sample, wherein the point is X if the sample has a high concentration of a cytokine which is positively associated with overall survival of the patient during the anti-cancer treatment or a low concentration of a cytokine which is negatively associated with overall survival of the patient during the anti-cancer treatment, wherein the point is Z if the sample has a low concentration of a cytokine which is positively associated with the overall survival of the patient during the anti-cancer treatment or a high concentration of a cytokine which is negatively associated with the overall survival of the patient during the anti-cancer treatment, and, optionally, wherein the point is Y if the sample has a medium concentration of a cytokine which is either negatively or positively associated with overall survival of the patient during the anti-cancer treatment.

E2. The method of embodiment E1, further comprising administering to the patient an anti-cancer treatment, wherein the cytokine score is higher than the average cytokine score.

E3. The method of embodiment E2, wherein the cytokine score is at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, at least about 95%, at least about 99% or 100% higher than the average cytokine score.

E4. The method of any one of embodiments E1 to E3, wherein X is any value, Z is a value that is lower than X, and, optionally, Y is a value that is between X and Z.

E5. The method of any one of embodiments E1 to E4, wherein Z is 0, Y is 1, and X is 2.

E6. The method of any one of embodiments E1 to E5, wherein the average cytokine score is any integer between 1 and 50, between 1 and 40, between 1 and 100, between 1 and 25, between 1 and 20, between 1 and 15, between 5 and 50, between 5 and 40, between 5 and 30, between 5 and 25, between 5 and 20, between 10 and 50, between 10 and 40, between 10 and 30, between 10 and 25, between 10 and 20, between 15 and 50, between 15 and 40, between 15 and 30, between 15 and 25, or between 15 and 20.

E7. The method of any one of embodiments E1 to E6, wherein the average cytokine score is 1, 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, about 50, about 60, about 70, about 80, about 90, or about 100.

E8. The method of any one of embodiments E1 to E7, wherein the at least one cytokine comprises at least two cytokines, at least three cytokines, at least four cytokines, at least five cytokines, at least six cytokines, at least seven cytokines, at least eight cytokines, at least nine cytokines, at least ten cytokines, at least 11 cytokines, at least 12 cytokines, at least 13 cytokines, at least 14 cytokines, at least 15 cytokines at least 16 cytokines, at least 17 cytokines, at least 18 cytokines, at least 19 cytokines, or at least 20 cytokines.

E9. The method of any one of embodiments E1 to E8, wherein the patient has lung cancer.

E10. The method of embodiment E9, wherein the lung cancer is non-small cell lung cancer.

E11. The method of embodiment E10, wherein the non-small cell lung cancer is squamous non-small cell lung cancer.

E12. The method of embodiment E10, wherein the non-small cell lung cancer is non-squamous non-small cell lung cancer.

E13. The method of any one of embodiments E1 to E11, wherein the at least one cytokine is selected from the group consisting of: MIG, IL-1RA, MMP-3, IL-8, FRTN, ICAM, VWF, MICA, IP-10, CRP, IL-18, VDBP, IL-6, MIP1B, and any combination thereof.

E14. The method of any one of embodiments E1 to E11) or E12, wherein the at least one cytokine is selected from the group consisting of: FRTN, MMP-3, IL-8, MCP2, ENRAGE, IL-2RA, IL-18, VWF, B2M, RANTES, MICA, TNFR2, VDBP, and any combination thereof.

E15. The method of any one of embodiments E1 to E11 or E13, wherein the positively associated cytokines are selected from the group consisting of MIG, IL-1RA, MMP-3, and any combination thereof.

E16. The method of any one of embodiments E1 to E11, E13 or E15, wherein the negatively associated cytokines are selected from the group consisting of IL-8, FRTN, ICAM, VWF, MICA, IP-10, CRP, IL-18, VDBP, IL-6, MIP1B, and any combination thereof.

E17. The method of any one of embodiments E1 to E10, E12 or E14, wherein the positively associated cytokines are B2M, VDBP, or both.

E18. The method of any one of embodiments E1 to E10, E12, E14 or E17, wherein the negatively associated cytokines are selected from the group consisting of: FRTN, MMP-3, IL-8, MCP2, ENRAGE, IL-2RA, IL-18, VWF, RANTES, MICA, TNFR2, and any combination thereof.

E19. The method of any one of embodiments E1 to E18, wherein the anti-cancer treatment is an effective amount of an anti-PD-1 antibody or antigen-binding portion thereof ("anti-PD-1 antibody") or an effective amount of an anti-PDL-1 antibody or antigen-binding portion thereof ("anti-PDL-1 antibody").

E20. The method of embodiment E19, wherein the anti-PD-1 antibodies cross-competes with a reference antibody which is nivolumab for binding to human PD-1.

E21. The method of embodiment E19 or E20, wherein the anti-PD-1 antibody comprises a heavy chain constant region which is of a human IgG1, IgG2, IgG3, or IgG4 isotype.

E22. The method of any one of embodiments E19 to E21, wherein the anti-PD-1 antibody is a chimeric, humanized or human monoclonal anti-PD-1 antibody or an antigen-binding portion thereof.

E23. The method of any one of embodiments E19 to E22, wherein the anti-PD-1 antibody is nivolumab.

E24. The method of any one of embodiments E19 to E22, wherein the anti-PD-1 antibody is pembrolizumab.

E25. The method of embodiment E19, wherein the anti-PD-L1 antibody crosses-competes with a reference antibody selected from the group consisting of BMS-936559, MPDL3280A, MEDI4736, and MSB0010718C for binding to human PD-L1.

E26. The method of embodiment E19 or E25, wherein the anti-PD-L1 antibody is selected from the group consisting of BMS-936559, MPDL3280A, MEDI4736, and MSB0010718C.

BRIEF DESCRIPTION OF THE DRAWINGS

FIGS. 2A-2F provide a model evaluation of selected cytokines in the validation set. The selected cytokines (FIG. 2A) were measured 6 months (FIG. 2B), 9 months (FIG. 2C), 12 months (FIG. 2D), 15 months (FIG. 2E), and 18 months (FIG. 2F) after treatment. AIC, Akaike information criterion. AUC, area under the curve.

FIGS. 4A-4J show the time-varying receiver-operating characteristic (ROC) analysis of selected cytokines in the training set (FIGS. 4A-4E) and validation set (FIGS. 4F-4J) of advanced or metastatic squamous cell non-small cell lung cancer patients.

FIGS. 10A-10J show the time-varying receiver-operating characteristic (ROC) analysis of selected cytokines in the training set (FIGS. 10A-10E) and validation set (FIGS. 10F-10J) of non-squamous non-small cell lung cancer patients.

DETAILED DESCRIPTION OF THE INVENTION

Figure 1:
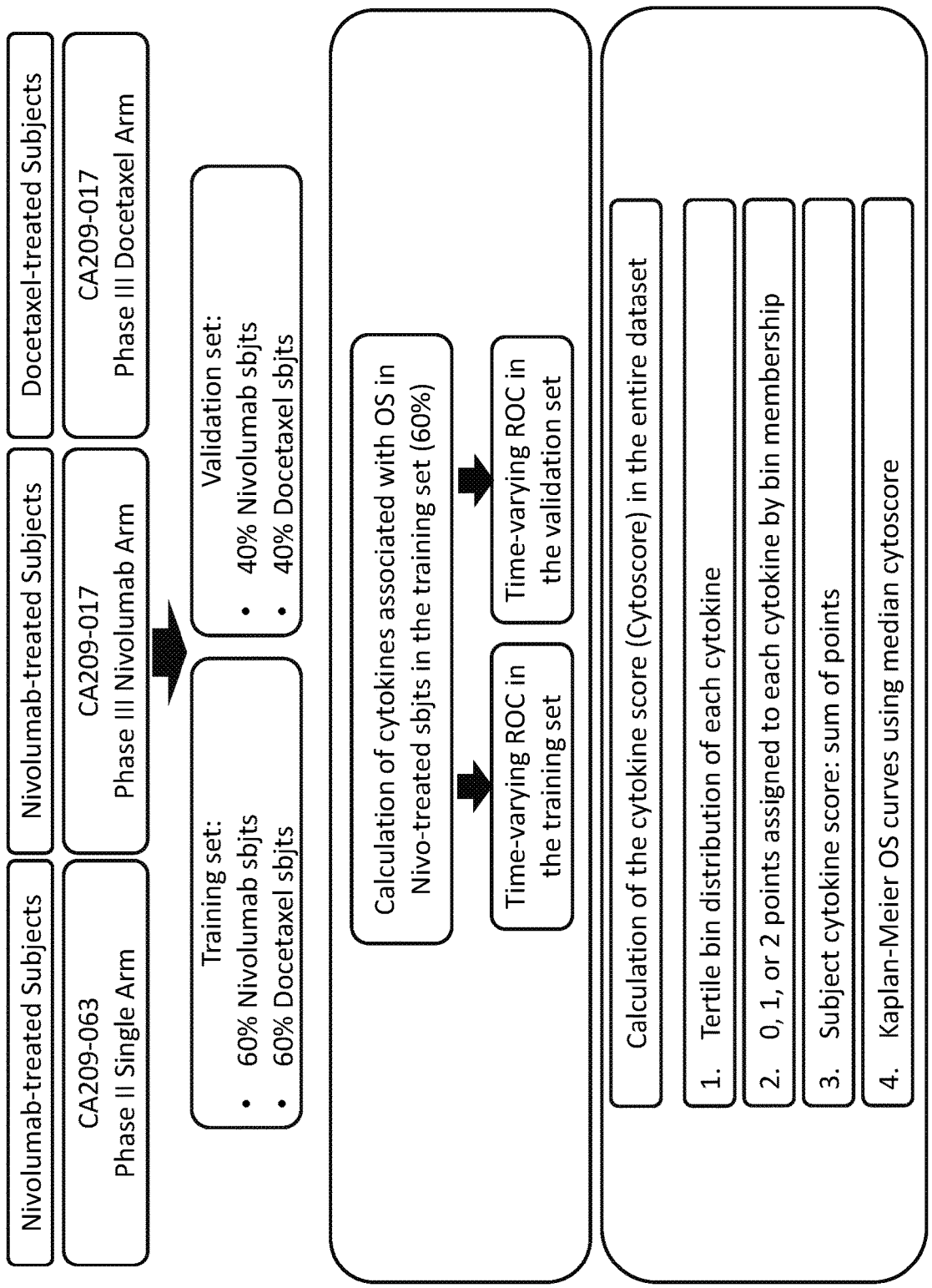
FIG. 1 shows a schematic of the method of determining cytokines associated with overall survival (OS) and calculating the cytoscore in patients with squamous cell non-small cell lung cancer. Sbjts, subjects; ROC, receiver-operating characteristic.

This invention relates to method of predicting a prognosis of a patient in need of an anti-cancer treatment comprising measuring cytokine concentrations and determining a cytokine score ("cytoscore") from a sample obtained from the patient. In certain embodiments, cytokines positively and/or negatively associated with overall survival (OS) are measured. In some embodiments, the subject is administered an anti-cancer treatment following the cytoscore measurement. In some embodiments, the cancer is lung cancer.

Terms

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a therapeutic agent to a subject, using any of the various methods and delivery systems known to those skilled in the art. Exemplary routes of administration for an anti-PD-1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent may be administered via a non-parenteral route, or orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

An immunoglobulin may derive from any of the commonly known isotypes, including but not limited to IgA, secretory IgA, IgG, and IgM. IgG subclasses are also well known to those in the art and include but are not limited to human IgG1, IgG2, IgG3, and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or non-human antibodies; wholly synthetic antibodies; and single chain antibodies. A non-human antibody may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 may, however, have cross-reactivity to other antigens, such as PD-1 molecules from different species. Moreover, an isolated antibody may be substantially free of other cellular material and/or chemicals.

The term "monoclonal antibody" (mAb) refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. Monoclonal antibodies may be produced by hybridoma, recombinant, transgenic, or other techniques known to those skilled in the art.

A "human antibody" (HuMAb) refers to an antibody having variable regions in which both the FRs and CDRs are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" and are used synonymously.

A "humanized antibody" refers to an antibody in which some, most, or all of the amino acids outside the CDRs of a non-human antibody are replaced with corresponding amino acids derived from human immunoglobulins. In one embodiment of a humanized form of an antibody, some, most, or all of the amino acids outside the CDRs have been replaced with amino acids from human immunoglobulins, whereas some, most, or all amino acids within one or more CDRs are unchanged. Small additions, deletions, insertions, substitutions, or modifications of amino acids are permissible as long as they do not abrogate the ability of the antibody to bind to a particular antigen. A "humanized antibody" retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen antibody" refers to an antibody that binds specifically to the antigen. For example, an anti-PD-1 antibody binds specifically to PD-1.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream. In some embodiments, the cancer is any cancer disclosed herein. In embodiments, the cancer is lung cancer. In certain embodiments, the lung cancer is non-small cell lung cancer (NSCLC). In embodiments, the NSCLC has a squamous histology (squamous NSCLC). In other embodiments, the NSCLC has a non-squamous histology (non-squamous NSCLC). A "cancer" can include a tumor. A "tumor" refers to all neoplastic cell growth and proliferation, whether malignant or benign, and all pre-cancerous and cancerous cells and tissues.

The term "immunotherapy" refers to the treatment of a subject afflicted with, at risk of contracting, or suffering a recurrence of a disease by a method comprising inducing, enhancing, suppressing, or otherwise modifying an immune response.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease.

"Programmed Death-1" (PD-1) refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1" (PD-L1) is one of two cell surface glycoprotein ligands for PD-1 (the other being PD-L2) that down regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or non-human animal. The term "non-human animal" includes, but is not limited to, vertebrates such as non-human primates, sheep, dogs, and rodents such as mice, rats and guinea pigs. In some embodiments, the subject is a human. The terms "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity or other adverse physiological effects at the cellular, organ, and/or organism level (adverse effects) resulting from administration of the drug.

By way of example for the treatment of tumors, a therapeutically effective amount of an anti-cancer agent inhibits cell growth or tumor growth by at least about 10%, at least about 20%, by at least about 30%, by at least about 40%, by at least about 50%, by at least about 60%, by at least about 70%, by at least about 80%, at least about 90%, at least about 95%, or at least about 100% relative to untreated subjects.

In other embodiments of the invention, tumor regression can be observed and continue for a period of at least about 20 days, at least about 30 days, at least about 40 days, at least about 50 days, or at least about 60 days. Notwithstanding these ultimate measurements of therapeutic effectiveness, evaluation of immunotherapeutic drugs must also make allowance for "immune-related response patterns".

As used herein, "outcome" or "clinical outcome" refers to the course of a disease and/or the disease progression. The clinical outcome can be characterized, for example, by recurrence, period of time until recurrence, metastasis, period of time until metastasis, number of metastases, number of sites of metastases, and/or death due to the disease.

An "immune-related response pattern" refers to a clinical response pattern often observed in cancer patients treated with immunotherapeutic agents that produce anti-tumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents may require long-term monitoring of the effects of these agents on the target disease.

A therapeutically effective amount of a drug includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The term "weight-based dose", as referred to herein, means that a dose administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

The use of the term "fixed dose" with regard to a method of the invention means that two or more different therapies in a single composition (e.g., anti-PD-1 antibody and another therapy) are present in the composition in particular (fixed) ratios with each other. In some embodiments, the fixed dose is based on the weight (e.g., mg) of the therapies, i.e., antibodies. In certain embodiments, the fixed dose is based on the concentration (e.g., mg/ml) of the therapies. In some embodiments, the ratio of two antibodies in a fixed dose composition is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-PD-1 antibody) to mg second antibody. For example, the 3:1 ratio of an anti-PD-1 antibody and a second antibody can mean that a vial can contain about 240 mg of the anti-PD-1 antibody and 80 mg of the second antibody or about 3 mg/ml of the anti-PD-1 antibody and 1 mg/ml of the second antibody.

The use of the term "flat dose" with regard to the methods and dosages of the invention means a dose that is administered to a patient without regard for the weight or body surface area (BSA) of the patient. The flat dose is therefore not provided as a mg/kg dose, but rather as an absolute amount of the agent (e.g., the anti-PD-1 antibody). For example, a 60 kg person and a 100 kg person would receive the same dose of an antibody (e.g., 240 mg of an anti-PD-1 antibody).

The term "measuring" or "measured" or "measurement" when referring to concentration or expression level of one or more cytokines refers to determining a measurable quantity and/or concentration of the cytokines in a sample of the subject. It will be appreciated that measuring can be performed on a nucleic acid gene product, such as mRNA or cDNA, or a protein. The measuring is performed on a subject's sample and/or a reference sample or samples and can, for example, be detected de novo or correspond to a previous determination. The measuring can be performed, for example, using microarray methods, PCR methods, antibody-based methods (including immunoassays), and/or any other method disclosed herein, as is known to a person of skill in the art.

The term "sample" or "biological sample" means biological material isolated from a subject. The biological sample can contain any biological material suitable for determining the concentration of a cytokine. The sample can be isolated from any suitable biological tissue or fluid such as, for example, tumor tissue, blood, blood plasma, serum, urine, or cerebral spinal fluid. In one embodiment, the sample is a blood serum sample.

The term "cytokine" refers to the category of small proteins (~5-20 kDa) that play a role in cell signaling. Cytokines can include, without limitation, chemokines, interferons, interleukins, monokines, lymphokines, colony stimulating factors, and tumour necrosis factors. Cytokines include those cytokines categorized by their structural characteristics, including, without limitation: 1) the four-α-helix bundle family (which includes three subfamilies: the IL-2 subfamily, the interferon (IFN) subfamily, and the IL-10 subfamily); 2) the IL-1 family; 3) the IL-17 family; and 4) the cysteine-knot cytokines. Cytokines also include those cytokines categorized by their functional characteristics, including, without limitation, immunological cytokines (type 1 enhances cellular responses and type 2 favors antibody responses) and inflammatory cytokines.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%, or up to 10%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range, or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

Methods of Cytokine Measurement for Prediction and Prognosis

The present invention is directed to a method of predicting the prognosis of a patient in need of an anti-cancer treatment comprising measuring a cytokine score from a sample obtained from the patient. The invention is, for example, directed to methods of increasing the prognosis of a patient in need of an anti-cancer treatment, e.g., an anti-PD-1 antibody treatment or an anti-PD-L1 antibody treatment, by selecting or identifying the patient's likelihood of responding to the anti-cancer treatment prior to the treatment. In one embodiment, the selection or identification of the suitable patients can be achieved by measuring the baseline cytokine level, either a high or low cytokine level at the baseline compared to a reference cytokine level. In another embodiment, the invention provides a method of measuring a cytokine level using a score matrix. While the present invention provides such a score matrix, e.g., cytokine score, the present invention is not limited to the particular score method, but can employ any other methods of measuring the cytokine level. The terms "cytokine score" and "cytoscore" are used interchangeably herein. The cytokine score is the sum of a point designated to the level of at least one cytokine in the sample. The point is X if the sample has (i) a high concentration of a cytokine that is positively associated with overall survival of the patients during the anti-cancer treatment, or (ii) a low concentration of a cytokine that is negatively associated with overall survival of the patients during the anti-cancer treatment. The point is Z if the sample has (i) a low concentration of a cytokine that is positively associated with the overall survival of the patients during the anti-cancer treatment, or (ii) a high concentration of a cytokine that is negatively associated with the overall survival of the patients during the anti-cancer treatment. Optionally, the point is Y if the sample has a medium concentration of a cytokine that is either negatively or positively associated with overall survival of the patients during the anti-cancer treatment. In some embodiments, the sample used to measure the cytokine concentrations is a blood serum sample. The present invention, therefore, can select a patient who would survive longer when treated with the anti-cancer treatment.

In some embodiments, the present invention is directed to a method of selecting a patient who would respond well to the anti-cancer treatment comprising measuring a cytokine score from a sample obtained from the patient, wherein the cytokine score is the sum of a point designated to the level of at least one cytokine in the sample. The point is X if the sample has (i) a high concentration of a cytokine that is positively associated with overall survival of the patients during the anti-cancer treatment, or (ii) a low concentration of a cytokine that is negatively associated with overall survival of the patients during the anti-cancer treatment. The point is Z if the sample has (i) a low concentration of a cytokine that is positively associated with the overall survival of the patients during the anti-cancer treatment, or (ii) a high concentration of a cytokine that is negatively associated with the overall survival of the patients during the anti-cancer treatment. Optionally, the point is Y if the sample has a medium concentration of a cytokine that is either negatively or positively associated with overall survival of the patients during the anti-cancer treatment. In some embodiments, the sample used to measure the cytokine concentrations is a blood serum sample. The present methods, therefore, can predict a clinical outcome of a human suffering from cancer.

In other embodiments, the invention is directed to a method for determining whether a tumor from a human is likely to respond to an anti-cancer treatment comprising determining the expression level of one or more cytokines of interest in tumor cells from the human, wherein the presence of a high expression level of one or more cytokines of interest indicates that the tumor is likely to respond to the anti-cancer treatment.

In some embodiments, a cytokine concentration is considered to be a "high concentration" if the cytokine concentration is at least about 0.1%, 1%, 2%, 3%, 5%, 6%, 7%, 8%, 9%, 10%, 15%, 20%, 25%, 30%, 40%, 50%, 60%, 70%, 75%, 80%, 90%, 95%, 99%, or 100% greater than the average concentration value. In certain embodiments, a cytokine concentration is considered to be a "low concentration" if the concentration is at least about 0.001%, 0.01%, 0.1%, 1%, 2%, 3%, 5%, 6%, 7%, 8%, 9%, 10%, 15%, 20%, 25%, 30%, 40%, 50%, 60%, 70%, 75%, 80%, 90%, 95%, 99%, or 100% lower than the average concentration value. In other embodiments, a cytokine concentration is considered to be a medium concentration if the concentration is at least about 5%, 10%, 15%, 20%, 25%, 30%, 40%, 50%, 60%, 70%, 75%, 80%, 90%, 95%, 99%, or 100% higher or lower than the average concentration value. In other embodiments, the concentration is medium if the concentration is 40% to 60% of the average concentration value. The "average concentration value" refers to the central or typical cytokine concentration in a set of data, e.g., a patient or patient group (which may be gender-matched, age-matched, etc.), in particular the mode, median, or mean, and can be calculated by dividing the sum of the values in the set by the number of entities in the set.

In one embodiment, the high concentrations of cytokines are divided into one, two, three, four, five, six, seven, eight, nine, ten or more concentration ranges, and each range is assigned a different point value. In another embodiment, the low concentrations of cytokines are divided into one, two, three, four, five, six, seven, eight, nine, ten or more concentration ranges, and each range is assigned a different point value. In a further embodiment, the medium concentrations of cytokines are divided into one, two, three, four, five, six, seven, eight, nine, ten or more concentration ranges, and each range is assigned a different point value. In one embodiment, there are two concentrations: one each of high and low concentrations. In a further embodiment, there are three concentration ranges: one each for high, medium, and low concentrations.

In some embodiments, the low concentration ranges, measured by custom HumanMAP quantitative multiplexed immunoassay, are as follows: between about 0.01 and about 3000, between about 0.01 and about 1000, between about 0.01 and about 750, between about 0.01 and about 500, between about 0.01 and about 250, between about 0.01 and about 100, between about 0.01 and about 50, between about 0.01 and about 25, between about 0.01 and about 10, between about 0.01 and about 5, between about 0.1 and about 3000, between about 0.1 and about 1000, between about 0.1 and about 750, between about 0.1 and about 500, between about 0.1 and about 250, between about 0.1 and about 100, between about 0.1 and about 50, between about 0.1 and about 25, between about 1 and about 3000, between about 1 and about 1000, between about 1 and about 750, between about 1 and about 500, between about 1 and about 250, between about 1 and about 100, between about 1 and about 50, between about 1 and about 25; between about 5 and about 3000, between about 5 and about 1000, between about 5 and about 750, between about 5 and about 500, between about 5 and about 250, between about 5 and about 100, between about 5 and about 50, between about 5 and about 25, between about 20 and about 3000, between about 20 and about 1000, between about 20 and about 750, between about 20 and about 500, between about 20 and about 250, between about 20 and about 100, between about 20 and about 50, between about 20 and about 25, between about 50 and about 3000, between about 50 and about 1000, between about 50 and about 750, between about 50 and about 500, between about 50 and about 250, between about 50 and about 100, between about 100 and about 3000, between about 100 and about 1000, between about 100 and about 750, between about 100 and about 500, between about 100 and about 250, between about 225 and about 3000, between about 225 and about 1000, between about 225 and about 750, between about 225 and about 500, and between about 225 and about 250.

In other embodiments, the medium concentration ranges, measured by custom HumanMAP quantitative multiplexed immunoassay, are as follows: between about 2 and about 4500, between about 2 and about 2000, between about 2 and about 1100, between about 2 and about 1000, between about 2 and about 750, between about 2 and about 500, between about 2 and about 250, between about 2 and about 100, between about 2 and about 50, between about 2 and about 25, between about 20 and about 4500, between about 20 and about 2200, between about 20 and about 1100, between about 20 and about 1000, between about 20 and about 750, between about 20 and about 500, between about 20 and about 250, between about 20 and about 100, between about 20 and about 50, between about 20 and about 25, between about 50 and about 4500, between about 50 and about 2200, between about 50 and about 1100, between about 50 and about 1000, between about 50 and about 750, between about 50 and about 500, between about 50 and about 250, between about 50 and about 100, between about 100 and about 4500, between about 100 and about 2200, between about 100 and about 1100, between about 100 and about 1000, between about 100 and about 750, between about 100 and about 500, between about 100 and about 250, between about 225 and about 4500, between about 225 and about 2200, between about 225 and about 1100, between about 225 and about 1000, between about 225 and about 750, between about 225 and about 500, between about 225 and about 250, between about 300 and about 4500, between about 300 and about 2200, between about 300 and about 1100, between about 300 and about 1000, between about 300 and about 750, between about 300 and about 500, between about 500 and about 4500, between about 500 and about 2200, between about 500 and about 1100, between about 500 and about 1000, between about 500 and about 750, between about 1000 and about 4500, between about 1000 and about 2200, between about 1500 and 4500, between about 1500 and 2200, between about 2000 and 4500, and between about 2000 and 2200.

In some embodiments, the high concentration ranges, measured by custom HumanMAP quantitative multiplexed immunoassay, are as follows: between about 2 and about 35000, between about 2 and about 25000, between about 2 and about 10000, between about 2 and about 5000, between about 2 and about 1000, between about 2 and about 500, between about 2 and about 250, between about 2 and about 150, between about 2 and about 100, between about 20 and about 35000, between about 20 and about 25000, between about 20 and about 10000, between about 20 and about 5000, between about 20 and about 1000, between about 20 and about 500, between about 20 and about 250, between about 20 and about 150, between about 20 and about 100, between about 50 and about 35000, between about 50 and about 25000, between about 50 and about 10000, between about 50 and about 5000, between about 50 and about 1000, between about 50 and about 500, between about 50 and about 250, between about 50 and about 150, between about 50 and about 100, between about 100 and about 35000, between about 100 and about 25000, between about 100 and about 10000, between about 100 and about 5000, between about 100 and about 1000, between about 100 and about 500, between about 100 and about 250, between about 100 and about 150, between about 200 and about 35000, between about 200 and about 25000, between about 200 and about 10000, between about 200 and about 5000, between about 200 and about 1000, between about 200 and about 500, between about 200 and about 250, between about 500 and about 35000, between about 500 and about 25000, between about 500 and about 10000, between about 500 and about 5000, between about 500 and about 1000, between about 1000 and about 35000, between about 1000 and about 25000, between about 1000 and about 10000, between about 1000 and about 5000, between about 2000 and about 35000, between about 2000 and about 25000, between about 2000 and about 10000, between about 2000 and about 5000, between about 5000 and about 35000, between about 5000 and about 25000, and between about 5000 and about 10000.

In a further embodiment, the concentration ranges, measured by custom HumanMAP quantitative multiplexed immunoassay, are as follows: IL-8 low: 0 to about 10, e.g., about 2.9 to about 10, medium: about 11 to about 21, high: about 22 or higher, e.g., about 22 to about 687; FRTN low: 0 to about 276, e.g., about 16 to about 276, medium: about 277 or about 282 to about 581, high: about 582 or higher, e.g., about 582 or about 583 to about 5090; ICAM1 low: 0 to about 135, e.g., about 3.2 to about 135; medium: about 136 to about 189; high: about 190 or higher, e.g., about 190 to about 625; VWF low: 0 to about 154, e.g., about 52 to about 154, medium: about 155 to about 219, high: about 220 or higher, e.g., about 220 to about 1660; MIG low: 0 to about 1120, e.g., about 235 to about 1120, medium: about 1121 or about 1130 to about 2040, high: about 2041 or about 2050 or higher, e.g., about 2050 to about 22800; IL-1RA low: 0 to about 413, e.g., about 296 to about 413, medium: about 414 or about 437 to about 755, high: about 756 or about 773 or higher, e.g., about 773 to about 2850; MICA low: 0 to about 47, e.g., about 4.7 to about 4.7 or about 4.7 to about 47; medium: about 48 or about 49 to about 75; high: about 76 or higher, e.g., about 80 to about 185; IP-10 low: 0 to about 232, e.g., about 112 to about 232; medium: about 233 or about 235 to about 365; high: about 366 or higher, e.g., about 366 or about 368 to about 8070; MMP-3 low: 0 to about 10, e.g., about 2.4 to about 10, medium: about 11 to about 19, high: about 20 or higher, e.g., about 20 to about 129; CRP low: 0 to about 23, e.g., about 0.36 to about 23, medium: about 24 or about 25 to about 86, high: about 87 or higher, e.g., about 87 to about 535; IL-18 low: 0 to about 219, e.g., about 52 to about 219, medium: about 220 to about 333, high: about 334 or higher, e.g., about 334 to about 33600; VDBP low: 0 to about 252, e.g., about 74 to about 252, medium: about 253 to about 343, high: about 344 or higher, e.g., about 344 to about 638; IL-6 low: 0 to about 4.4, e.g., about 0.8 to about 4.4, medium: about 4.5 to about 5.4; high: about 5.5 or higher, e.g., about 5.5 to about 181; MIP1B low: 0 to about 156, e.g., about 30 to about 156, medium: about 157 to about 254, high: about 255 or higher, e.g., about 255 to about 3380, and the cancer is squamous non-small cell lung cancer. In one embodiment, the concentration ranges relate to a SQ-Cytoscore.

In an embodiment, the concentration ranges, measured by custom HumanMAP quantitative multiplexed immunoassay, are as follows: FRTN low: 0 to about 223, e.g., about 20 to about 223, medium: about 224 to about 489, high: about 490 or higher, e.g., about 490 to about 4020; MMP-3 low: 0 to about 10, e.g., about 0.084 to about 10, medium: about 11 to about 22, high: about 23 or higher, e.g., about 23 to about 98; IL-8 low: 0 to about 9.2, e.g., about 2.9 to about 9.2, medium: about 9.3 to about 18, high: about 19 or higher, e.g., about 19 to about 480; MCP2 low: 0 to about 46, e.g., about 17 to about 46, medium: about 47 to about 60, high: about 61 or higher, e.g., about 61 to about 628; ENRAGE low: 0 to about 73, e.g., about 2.5 to about 73, medium: about 74 to about 172, high: about 173 or higher, e.g., about 173 to about 2720; IL-2RA low: 0 to about 2480, e.g., about 298 to about 2840, medium: about 2850 to about 4210, high: about 4230 or higher, e.g., about 4230 to about 19900; IL-18 low: 0 to about 204, e.g., about 12 to about 204, medium: about 205 to about 298, high: about 299 or higher, e.g., about 299 to about 1540; VWF low: 0 to about 130, e.g., about 5.8 to about 130, medium: about 131 to about 195, high: about 198 or higher, e.g., about 198 to about 826; B2M low: 0 to about 2.1, e.g., about 0.13 to about 2.1, medium: about 2.2 to about 2.9, high: about 3 or higher, e.g., about 3 to about 7.9; RANTES low: 0 to about 15, e.g., about 0.049 to about 15, medium: about 16 to about 27, high: about 28 or higher, e.g., about 28 to about 89; MICA medium: about 4.7 to about 47, e.g., about 47 to about 47, high: about 48 or higher, e.g., about 48 to about 718; TNFR2 low: 0 to about 6.7, e.g., about 1 to about 6.7, medium: about 6.8 to about 9.7, high: about 9.8 or higher, e.g., about 9.8 to about 41; VDBP low: 0 to about 269, e.g., about 9.8 to about 269, medium: about 270 to about 372, high: about 373 or higher, e.g., about 373 to about 676, and the cancer is non-squamous non-small cell lung cancer. In one embodiment, the concentration ranges relate to a NSQ-Cytoscore.

In other embodiments, the concentration ranges, measured by custom HumanMAP quantitative multiplexed immunoassay, are as follows: IL8 low: about 2.9-about 10, medium: about 11-about 21, high: about 22-about 687; FRTN low: about 16-about 276, medium: about 282-about 581, high about 583-about 5090; ICAM1 low: about 3.2-about 135; medium: about 136-about 189; high: about 190-about 625; VWF low: about 52-about 154, medium: about 155-about 219, high: about 220-about 1660; MIG low: about 235-about 1120, medium: about 1130-about 2040, high: about 2050-about 22800; IL1RA low: about 296-about 413, medium: about 437-about 755, high: about 773-about 2850; MICA: low: about 4.7-about 4.7; medium: about 5-about 75; high: about 80-about 185; IP10 low: about 112-about 232; medium: about 235-about 365; high: about 368-about 8070; MMP3 low: about 2.4-about 10, medium: about 11-about 19, high about 20-about 129; CRP low: about 0.36-about 23, medium: about 25-about 86, high: about 87-about 535; IL18 low: about 52-about 219, medium: about 220-about 333, high: about 334-about 33600; VDBP low: about 74-about 252, medium: about 253-about 343, high: about 344-about 638; IL6 low: about 0.8-about 4.4, medium about 4.5-about 5.4; high: about 5.5-about 181; MIP1B low: about 30-about 156, medium: about 157-about 254, high: about 255-about 3380, and the cancer is squamous non-small cell lung cancer.

In an embodiment, the concentration ranges, measured by custom HumanMAP quantitative multiplexed immunoassay, are as follows: FRTN low: about 20-about 223, medium: about 224-about 489, high: about 490-about 4020; MMP3 low: about 0.084-about 10, medium: about 11-about 22, high: about 23-about 98; IL8 low: about 2.9-about 9.2, medium: about 9.3-about 18, high: about 19-about 480; MCP2 low: about 17-about 46, medium: about 47-about 60, high: about 61-about 628; ENRAGE low: about 2.5-about 73, medium: about 74-about 172, high: about 173-about 2720; IL2RA low: about 298-about 2840, medium: about 2850-about 4210, high: about 4230-about 19900; IL18 low: about 12-about 204, medium: about 205-about 298, high: about 299-about 1540; VWF low: about 5.8-about 130, medium: about 131-about 195, high: about 198-about 826; B2M low: about 0.13-about 2.1, medium: about 2.2-about 2.9, high: about 3-about 7.9; RANTES low: about 0.049-about 15, medium: about 16-about 27, high: about 28-about 89; MICA medium: about 47-about 47, high: about 48-about 718; TNFR2 low: about 1-about 6.7, medium: about 6.8-about 9.7, high: about 9.8-about 41; VDBP low: about 9.8-about 269, medium: about 270-about 372, high: about 373-about 676 and the cancer is nonsquamous non-small cell lung cancer.

In certain embodiments, X is any value, Z is a value that is lower than X, and, optionally, Y is a value that is between X and Z. In an embodiment, Z is any value, X is the value Z+1, Z+2, Z+3, Z+4, Z+5, Z+6, Z+7, Z+8, Z+9, Z+10, Z+25, Z+50, Z+100, or any greater value, and Y is any value between Z and X. In one embodiment, Z is any value, Y is the value Z+1, Z+2, Z+3, Z+4, Z+5, Z+6, Z+7, Z+8, Z+9, Z+10, Z+25, Z+50, Z+100, or any greater value, and X is the value Y+1, Y+2, Y+3, Y+4, Y+5, Y+6, Y+7, Y+8, Y+9, Y+10, Y+25, Y+50, Y+100, or any greater value. In particular embodiments, Z is 0, Y is 1, and X is 2.

In other embodiments, the average cytoscore is any integer between 1 and 50, between 1 and 40, between 1 and 100, between 1 and 25, between 1 and 20, between 1 and 15, between 5 and 50, between 5 and 40, between 5 and 30, between 5 and 25, between 5 and 20, between 10 and 50, between 10 and 40, between 10 and 30, between 10 and 25, between 10 and 20, between 15 and 50, between 15 and 40, between 15 and 30, between 15 and 25, or between 15 and 20. In certain embodiments, the average cytoscore is 1, 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, about 50, about 60, about 70, about 80, about 90, or about 100.

In some embodiments, a cytoscore is characterized as a "high" cytoscore or a "low" cytoscore based on the median cytoscore cutoff for all patients. In some embodiments, a cytoscore at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, at least about 95%, at least about 99%, or 100% higher than the median cytoscore cutoff is characterized as a "high" cytoscore. In certain embodiments, a cytoscore at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, at least about 95%, at least about 99%, or 100% lower than the median cytoscore cutoff is characterized as a "low" cytoscore. In some embodiments, the cytoscores of the invention are higher than the median cytoscore. The "median cytoscore" refers to the cytoscore lying at the midpoint of a frequency distribution of observed cytoscore values in a set of data, e.g., a patient or patient group (which may be gender-matched, age-matched, etc.), such that there is an equal probability of falling above or below it.

In certain embodiments, the concentrations of the cytokines and/or the cytoscores are used to predict the overall survival of a patient with cancer. In certain embodiments, the concentrations of the cytokines and/or the cytoscores are used to predict the clinical outcome of a patient with cancer. In some embodiments, the concentrations of the cytokines and/or the cytoscores are used to determine whether or not a patient with cancer will be responsive to an anti-cancer treatment. In certain embodiments, patients with high cytoscores have a longer overall survival than patients with low cytoscores when administered the same treatment.

In some embodiments, any known cytokine is measured. In certain embodiments, one or more cytokines are positively associated with overall survival. In other embodiments, one or more cytokines are negatively associated with overall survival. In further embodiments, one or more cytokines positively associated with overall survival are measured and one or more cytokines negatively associated with overall survival are measured.

In some embodiments, the cytokines are one or more, two or more, three or more, four or more, five or more, six or more, seven or more, eight or more, nine or more, ten or more, eleven or more, twelve or more, thirteen or more, or fourteen or more cytokines selected from the group consisting of MIG, IL-1RA, MMP-3, IL-8, FRTN, ICAM, VWF, MICA, IP-10, CRP, IL-18, VDBP, IL-6, MIP1B, and any combination thereof. In certain embodiments, the cytokines are one or more, two or more, or three cytokines selected from the group consisting of MIG, IL-1RA, MMP-3, and any combination thereof, and are positively associated with overall survival. In certain embodiments, the cytokines are one or more, two or more, three or more, four or more, five or more, six or more, seven or more, eight or more, nine or more, ten or more, or eleven cytokines selected from the group consisting of IL-8, FRTN, ICAM, VWF, MICA, IP-10, CRP, IL-18, VDBP, IL-6, MIP1B and any combination thereof, and the cytokines are negatively associated with overall survival. In certain embodiments, the cancer is squamous non-small cell lung cancer.

In some embodiments, the cytokines are one or more, two or more, three or more, four or more, five or more, six or more, seven or more, eight or more, nine or more, ten or more, eleven or more, twelve or more, or thirteen cytokines selected from the group consisting of FRTN, MMP-3, IL-8, MCP2, ENRAGE, IL-2RA, IL-18, VWF, B2M, RANTES, MICA, TNFR2, VDBP, and any combination thereof. In certain embodiments, the cytokines are one or more of, or both of, B2M and VDBP, and the cytokines are positively associated with overall survival. In certain embodiments, the cytokines are one or more, two or more, three or more, four or more, five or more, six or more, seven or more, eight or more, nine or more, ten or more, or eleven cytokines selected from the group consisting of FRTN, MMP-3, IL-8, MCP2, ENRAGE, IL-2RA, IL-18, VWF, RANTES, MICA, TNFR2, and any combination thereof, and the cytokines are negatively associated with overall survival. In other embodiments, the cancer is non-squamous non-small cell lung cancer.

In certain embodiments, the cytokine concentration is measured using any known method in the art. In some embodiments, the cytokines are measured using microarray methods, PCR methods, antibody-based methods (including immunoassays), and/or any other method disclosed herein, as is known to a person of skill in the art. In certain embodiments, the cytokines are measured using an immunoassay method. In further embodiments, the immunoassay method is a quantitative multiplexed immunoassay. In still a further embodiment, the quantitative multiplexed immunoassay is a custom HumanMAP quantitative multiplexed immunoassay.

In some embodiments, the baseline cytokine concentrations are measured prior to administration of one or more anti-cancer therapies. In other embodiments, cytokine concentrations are measured during the administration of one or more anti-cancer therapies. In further embodiments, cytokine concentrations are measured following the administration of one or more anti-cancer therapies.

In some embodiments, the invention is directed to determining cytokines that are positively and negatively associated with overall survival. In certain embodiments, the concentrations of evaluable cytokines are measured, and cytokines associated with overall survival are identified using statistical models. In certain embodiments, multivariate analysis is performed to identify cytokines associated with overall survival. In particular embodiments, the multivariate analysis is a stepwise variable selection methodology performed in a Cox model. In certain embodiments, the Kaplan-Meier method is used.

In some embodiments, the cancer is any cancer disclosed herein. Representative examples of cancers include melanoma (e.g., metastatic malignant melanoma), renal cancer, prostate cancer, breast cancer, colon cancer, and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, and combinations of said cancers. The present invention is also useful for treatment of metastatic cancers. In some embodiments, the cancer is colorectal cancer, rectal cancer, colon cancer, lung cancer, melanoma, ovarian cancer, head and neck cancer, or any combination thereof. In certain embodiments, the cancer is lung cancer. In particular embodiments, the cancer is non-small cell lung cancer (NSCLC). In particular embodiments, the NSCLC has a squamous histology. In other embodiments, the NSCLC has a non-squamous histology.

Treatment Methods of the Invention

The present invention is directed to a method for treating a cancer or a subject afflicted with cancer following measurement of cytokine concentrations that are positively and/or negatively associated with overall survival and a determination of the cytoscore. In some embodiments, subjects with cytoscores higher than the median cytoscore are administered any anti-cancer treatment disclosed herein. In certain embodiments, the cytoscore is at least about 0.1%, at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, at least about 95%, at least about 99%, or 100% higher than the average cytoscore. In other embodiments, subjects with cytoscores lower than the average cytoscore are administered anti-cancer treatments. In certain embodiments, the cytoscore is at least about 0.1%, at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, at least about 95%, at least about 99%, or 100% lower than the average cytoscore. The "average cytoscore" refers to the central or typical cytokine concentration in a set of data, e.g., a patient or patient group (which may be gender-matched, age-matched, etc.), in particular the mode, median, or mean, and can be calculated by dividing the sum of the values in the set by the number of entities in the set.

In certain embodiments, the cancer or subject afflicted with cancer whose cytoscore is measured is treated with any known standard of care therapy, including any therapy disclosed herein. In some embodiments, the cancer or subject afflicted with cancer is treated with an antibody or an antigen-binding portion thereof that binds specifically to a Programmed Death-1 (PD-1) receptor and inhibits PD-1 activity ("anti-PD-1 antibody"). In certain embodiments, the method of treating comprises administering to the subject a therapeutically effective amount of an anti-PD-1 antibody, wherein the anti-PD-1 antibody is administered in accordance with a treatment regimen determined from quantifying the cytoscore and/or baseline serum cytokine concentrations in a sample from said subject. In some embodiments, the subject is optionally treated with a second anti-cancer agent or therapy.

In certain embodiments, the subject is treated with any therapy or combination of therapies disclosed in U.S. Pat. No. 7,595,048 or 8,008,449; Int'l Appl. Nos. PCT/US2015/18727, PCT/US2015/031241 or PCT/US2015/066177; or U.S. Provisional Application Nos. 62/149,325; 62/265,268; 62/269,000; 62/303,855; 62/152,669; 62/153,954; 62/153,973; 62/167,674; 62/192,396; 62/216,265; 62/257,139; 62/268,991; or 62/173,247, each of which is incorporated herein in its entirety.

Representative examples of cancers for treatment with the therapies of the instant disclosure include melanoma (e.g., metastatic malignant melanoma), renal cancer, prostate cancer, breast cancer, colon cancer, and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, and combinations of said cancers. The present invention is also useful for treatment of metastatic cancers. In some embodiments, the cancer is colorectal cancer, rectal cancer, colon cancer, lung cancer, melanoma, ovarian cancer, head and neck cancer, or any combination thereof. In certain embodiments, the cancer is lung cancer.

In certain embodiments, the subject has received one, two, three, four, five or more prior cancer treatments. In other embodiments, the subject is treatment-naïve. In some embodiments, the subject has progressed on other cancer treatments. In some embodiments, the cancer has reoccurred. In some embodiments, the cancer is metastatic. In other embodiments, the cancer is not metastatic.

In certain embodiments, the lung cancer is non-small cell lung cancer (NSCLC). In some embodiments, the NSCLC has a squamous histology. In other embodiments, the NSCLC has a non-squamous histology. In yet other embodiments, the NSCLC has a squamous adenosquamous histology. In further embodiments, the NSCLC has a histology that is not otherwise specified. In certain embodiments, the malignancy is unresectable. In some embodiments, the NSCLC EGFR mutated.

In some embodiments, the head and neck cancer is recurrent or metastatic or recurrent SCCHN (oral cavity, pharynx, or larynx). In certain embodiments, the head and neck cancer is stage III/IV. In some embodiments, the cancer has progressed or reoccurred within six months of the last dose of platinum therapy. In some embodiments, the cancer is therapy-refractory.

In some embodiments, the ovarian cancer is recurrent or persistent epithelial ovarian, fallopian tube, or primary peritoneal carcinoma. In some embodiments, the subjects received a platinum and/or taxane-based chemotherapy regimen as their frontline therapy for ovarian cancer.

In some embodiments, the colorectal cancer is histologically confirmed. In certain embodiments, the colorectal cancer is metastatic or recurrent. In some embodiments, the subject has had progression during, after, or been intolerant following the last administration of standard therapies. In certain embodiments, the subject has microsatellite instability. In other embodiments, the colorectal cancer has low microsatellite instability (MSI-L).

In some embodiments, the cancer is microsatellite stable (MSS) (or "MSI stable") and therefore has no microsatellite instability. Microsatellite instability is the condition of genetic hypermutability that results from impaired DNA mismatch repair (MMR). The presence of MSI represents phenotypic evidence that MMR is not functioning normally. In most cases, the genetic basis for instability in MSI tumors is an inherited germline alteration in any one of the five human MMR genes: MSH2, MLH1, MSH6, PMS2, and PMS1. In certain embodiments, the subject receiving tumor treatment has no instability (MSS or MSI stable) and has no mutation in genes MSH2, MLH1, MSH6, PMS2, and PMS1. In other embodiments, the subject has MSI-L. In embodiments, the patient is MSI stable.

The PD-L1 status of a tumor in a subject can be measured prior to administering any composition or utilizing any method disclosed herein. PD-L1 expression can be determined by any methods known in the art.

In order to assess the PD-L1 expression, in one embodiment, a test tissue sample can be obtained from the patient who is in need of the therapy. In another embodiment, the assessment of PD-L1 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. It should also be understood that in certain embodiments the "measuring" or "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other healthcare provider for use in selecting a suitable candidate for the anti-PD-1 antibody or anti-PD-L1 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In some embodiments, PD-L1 expression is assayed by IHC. In other embodiments of all of these methods, cell surface expression of PD-L1 is assayed using, e.g., IHC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FM), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, "In vivo imaging in cancer," *Cold Spring Harb. Perspect. Biol.* 2(12): a003848 (2010)). Antibody specificity, coupled with the sensitivity and resolution of PET, makes immunoPET imaging particularly attractive for monitoring and assaying expression of antigens in tissue samples (McCabe and Wu, "Positive progress in immunoPET—not just a coincidence," *Cancer Biother. Radiopharm.* 25(3):253-61 (2010); Olafsen et al., "ImmunoPET imaging of B-cell lymphoma using 124I-anti-CD20 scFv dimers (diabodies)," *Protein Eng. Des. Sel.* 23(4):243-9 (2010)). In certain embodiments of any of the present methods, PD-L1 expression is assayed by immunoPET imaging. In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In other embodiments, the presence of PD-L1 polypeptide is determined by IHC assay. In further embodiments, the IHC assay is performed using an automated process. In some embodiments, the IHC assay is performed using an anti-PD-L1 monoclonal antibody to bind to the PD-L1 polypeptide.

In one embodiment of the present methods, an automated IHC method is used to assay the expression of PD-L1 on the surface of cells in FFPE tissue specimens. This disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a monoclonal antibody that specifically binds to human PD-L1, under conditions that allow for formation of a complex between the antibody or portion thereof and human PD-L1. In certain embodiments, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary antibody; incubating with a post primary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1+ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%. In one embodiment, the threshold number of cells that needs to be PD-L1 positive is at least about 100, at least about 125, at least about 150, at least about 175, or at least about 200 cells. In certain embodiments, the threshold number or cells that needs to be PD-L1 positive is at least about 100 cells.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently, and the scores are subsequently consolidated. In certain other embodiments, the identification of positive and negative cells is scored using appropriate software.

A histoscore is used as a more quantitative measure of the IHC data. The histoscore is calculated as follows:

$$Histoscore = [(\% \text{ tumor} \times 1 \text{ (low intensity)}) + (\% \text{ tumor} \times 2 \text{ (medium intensity)}) + (\% \text{ tumor} \times 3 \text{ (high intensity)})]$$

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., "Colocalization of inflammatory response with B7-hl expression in human melanocytic lesions supports an adaptive resistance mechanism of immune escape," *Sci. Transl. Med.* 4(127):127ra37 (2012)).

In one embodiment, the PD-L1 expression level of a tumor is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100%. In another embodiment, the PD-L1 status of a tumor is at least about 1%. In other embodiments, the PD-L1 status of the subject is at least about 5%. In a certain embodiment, the PD-L1 status of a tumor is at least about 10%. In a one embodiment, the PD-L1 status of the tumor is at least about 25%. In a particular embodiment, the PD-L1 status of the tumor is at least about 50%.

"PD-L1 positive" as used herein can be interchangeably used with "PD-L1 expression of at least about 1%". In one embodiment, the PD-L1 positive tumors can thus have at least about 1%, at least about 2%, at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of the tumor cells expressing PD-L1 as measured by an automated IHC. In certain embodiments, "PD-L1 positive" means that there are at least 100 cells that express PD-L1 on the surface of the cells.

In certain embodiments, the melanoma is advance disease (previously treated, therapy-refractory, or recurrent Stage III (unresectable) or Stage IV). In some embodiments, the patient with melanoma has a known BRAF V600 mutation. In certain embodiments, the patient has melanoma that is no longer controlled by surgery, chemotherapy or radiotherapy. In some embodiments, the patient has melanoma that is refractory to or relapsed after surgery. In other embodiments, the patient is treatment-naïve.

In certain embodiments, the overall survival of patients with high cytoscores is longer than patients with low cytoscores administered the same therapy or combination of therapies. In some embodiments, the overall survival of a patient with a high cytoscore is at least about 1 month, 2 months, 3 months, 4 months, 5 months, 6 months, 7 months, 8 months, 9 months, 10 months, 11 months, 1 year, or more than 1 year longer than a patient with a low cytoscore administered the same therapy or combination of therapies.

In other embodiments, the present methods comprise administering an effective amount of an anti-PD-1 antibody to a patient whose cytokines concentrations have been measured. In some embodiments, the patient has a high cytoscore. In one embodiment, the patient has a cytoscore that is higher than the median cytoscore. An effective amount of an anti-PD-1 antibody can be a flat dose or a weight-based dose.

In some embodiments, the invention includes a method of treating a cancer or a patient afflicted with cancer with a high cytoscore or a cytoscore that is higher than the median cytoscore, comprising administering an anti-PD-1 antagonist, and, optionally, a second anti-cancer agent to treat cancer. An "anti-PD-1 antagonist" as referred to herein includes any molecule that inhibits interaction between PD-1 (receptor) and PD-L1 (ligand) such that the signaling pathway of PD-1/PD-L1 is blocked. In other embodiments, an anti-PD-1 antagonist is a PD-1-Fc fusion protein. In certain embodiments, an anti-PD-1 antagonist includes an anti-PD-1 fusion protein, an antisense molecule, a small molecule, a ribozyme, or a nanobody that inhibits or prevents interaction between PD-1 and PD-L1.

In some embodiments, subjects with a high cytoscore treated with an anti-PD-1 antibody have an overall survival that is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 1 year or longer than subjects with a high cytoscore that are treated with a standard of care chemotherapy.

In certain embodiments, the methods of treatment of the present invention (e.g., administration of an anti-PD-1 antibody) effectively increases the duration of survival of the subject. For example, the duration of survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 1 year or more when compared to a subject having the same or similar cytoscore, but treated with another therapy, e.g., a standard of care therapy, or a subject having a low cytoscore (if patients with a high cytoscore are suitable for the anti-PD-1 antibody therapy), but treated with the same therapy. In certain embodiments, the therapy of the present invention effectively increases the duration of progression-free survival of the subject. For example, the progression-free survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 1 year when compared to a subject having the same or similar cytoscore, but treated with another therapy, e.g., a standard of care therapy, or a subject having a low cytoscore (if patients with a high cytoscore are suitable for the anti-PD-1 antibody therapy), but treated with the same therapy. In certain embodiments, the therapy of the present invention effectively increases the response rate in a group of subjects. For example, the response rate in a group of subjects is increased by at least about 2%, at least about 3%, at least about 4%, at least about 5%, at least about 10%, at least about 15%, at least about 20%, at least about 25%, at least about 30%, at last about 35%, at least about 40%, at least about 45%, at least about 50%, at least about 55%, at least about 60%, at least about 70%, at least about 75%, at least about 80%, at least about 85%, at least about 90%, at least about 95%, at least about 99%, or at least about 100% when compared to a subject having the same or similar cytoscore, but treated with another therapy, e.g., a standard of care therapy, or a subject having a low cytoscore (if patients with a high cytoscore are suitable for the anti-PD-1 antibody therapy), but treated with the same therapy.

In some embodiments, the anti-PD-1 antibody is formulated for intravenous administration. In certain embodiments, the anti-PD-1 and the optional second therapy are administered sequentially. In certain embodiments, the anti-PD-1 and the optional second therapy are administered within 30 minutes of each other. In one embodiment, the anti-PD-1 antibody or antigen-binding portion thereof is administered before the optional second therapy. In another embodiment, and the optional second therapy is administered before the anti-PD-1 antibody or antigen-binding portion thereof. In another embodiment, the anti-PD-1 antibody or antigen-binding portion thereof and the optional second therapy are administered concurrently in separate compositions. In a further embodiment, the anti-PD-1 antibody or antigen-binding portion thereof and the optional second therapy are admixed as a single composition for concurrent administration. In some embodiments, the anti-PD-1 antibody and the optional second therapy are administered in a fixed dose.

Anti-PD-1 Antibodies

The therapy of the present invention can utilize an anti-PD-1 antibody or an antigen-binding fragment thereof. PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Human monoclonal antibodies that bind specifically to PD-1 with high affinity have been disclosed in U.S. Pat. No. 8,008,449. Other anti-PD-1 monoclonal antibodies have been described in, for example, U.S. Pat. Nos. 6,808,710, 7,488,802, 8,168,757 and 8,354,509, and PCT Publication No. WO 2012/145493. Each of the anti-PD-1 human monoclonal antibodies disclosed in U.S. Pat. No. 8,008,449 has been demonstrated to exhibit one or more of the following characteristics: (a) binds to human PD-1 with a $K_D$ of $1\times10^{-7}$M or less, as determined by surface plasmon resonance using a Biacore biosensor system; (b) does not substantially bind to human CD28, CTLA-4, or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and/or (j) inhibits tumor cell growth in vivo. Anti-PD-1 antibodies usable in the present invention include monoclonal antibodies that bind specifically to human PD-1 and exhibit at least one, at least two, at least three, at least four, or at least five of the preceding characteristics.

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9): 846-56). Nivolumab has shown activity in a variety of advanced solid tumors including renal cell carcinoma (renal adenocarcinoma, or hypernephroma), melanoma, and non-small cell lung cancer (NSCLC) (Topalian et al., 2012a; Topalian et al., 2014; Drake et al., 2013; WO 2013/173223). In another embodiment, the anti-PD-1 antibody (or antigen-binding portion thereof) cross-competes with nivolumab. In some embodiments, the anti-PD-1 antibody binds to the same epitope as nivolumab. In certain embodiments, the anti-PD-1 antibody has the same CDRs as nivolumab.

In another embodiment, the anti-PD-1 antibody (or antigen-binding portion thereof) cross-competes with pembrolizumab. In some embodiments, the anti-PD-1 antibody binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also http://www.cancer.gov/drugdictionary?cdrid=695789 (last accessed: Dec. 14, 2014). Pembrolizumab has been approved by the FDA for the treatment of relapsed or refractory melanoma and advanced NSCLC.

In other embodiments, the anti-PD-1 antibody (or antigen-binding portion thereof) cross-competes with MEDI0680. In some embodiments, the anti-PD-1 antibody binds to the same epitope as MEDI0680. In certain embodiments, the anti-PD-1 antibody has the same CDRs as MEDI0680. In other embodiments, the anti-PD-1 antibody is MEDI0680 (formerly AMP-514), which is a monoclonal antibody against the PD-1 receptor. MEDI0680 is described, for example, in U.S. Pat. No. 8,609,089B2 or in http://www.cancer.gov/drugdictionary?cdrid=756047 (last accessed Dec. 14, 2014).

In certain embodiments, an immune checkpoint inhibitor is AMP-224, which is a B7-DC Fc fusion protein. AMP-224 is discussed in U.S. Publ. No. 2013/0017199 or in http://www.cancer.gov/publications/dictionaries/cancer-drug?cdrid=700595 (last accessed Jul. 8, 2015).

In other embodiments, the anti-PD-1 antibody (or antigen-binding portion thereof) cross-competes with BGB-A317. In some embodiments, the anti-PD-1 antibody binds to the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

Anti-PD-1 antibodies usable in the disclosed methods also include isolated antibodies that bind specifically to human PD-1 and cross-compete for binding to human PD-1 with nivolumab (see, e.g., U.S. Pat. No. 8,008,449; and WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays, or flow cytometry (see, e.g., WO 2013/173223).

In certain embodiments, the antibodies that cross-compete for binding to human PD-1 with nivolumab, or bind to the same epitope region of human PD-1 as nivolumab, are monoclonal antibodies. For administration to human subjects, these cross-competing antibodies can be chimeric antibodies, or can be humanized or human antibodies. Such chimeric, humanized, or human monoclonal antibodies can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, or (v) any combination thereof.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation, which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014). In yet other embodiments, the antibody comprises a light chain constant region which is a human kappa or lambda constant region. In other embodiments, the anti-PD-1 antibody or antigen-binding portion thereof is a monoclonal antibody or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3, and 5F4 described in U.S. Pat. No. 8,008,449. In still other embodiments, the anti-PD-1 antibody is MEDI0680 (formerly AMP-514), AMP-224, or BGB-A317.

In other embodiments, the anti-PD-1 antibody or antigen-binding portion thereof is a chimeric, humanized, or human monoclonal antibody or a portion thereof. In certain embodiments for treating a human subject, the antibody is a humanized antibody. In other embodiments for treating a human subject, the antibody is a human antibody. Antibodies of an IgG1, IgG2, IgG3, or IgG4 isotype may be used.

Because anti-PD-1 and anti-PD-L1 target the same signaling pathway and have been shown in clinical trials to exhibit similar levels of efficacy in a variety of cancers, an anti-PD-L1 antibody can be substituted for the anti-PD-1 antibody in any of the therapeutic methods or compositions disclosed herein. For example, an anti-PD-L1 antibody prevents interaction between PD-1 and PD-L1 and, thus, exerts similar effects to the signaling pathway of PD-1. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446 and atezolizumab) (see, e.g., Herbst; U.S. Pat. No. 8,217,149) or MEDI4736 (Khleif, 2013).

Anti-PD-L1 Antibodies

The therapy of the present invention can utilize an anti-PD-L1 antagonist (e.g., anti-PD-L1 antibody or an antigen binding portion thereof).

In other embodiments, the anti-PD-L1 antibody is BMS-936559 (formerly 12A4 or MDX-1105) (see, e.g., U.S. Pat. No. 7,943,743; and WO 2013/173223) or any other anti-PD-L1 antibody disclosed in U.S. Pat. No. 7,943,743. In some embodiments, the anti-PD-L1 antibody is an antibody that cross-competes with BMS-936559 for binding or the anti-PD-L1 antibodies disclosed in U.S. Pat. No. 7,943,743. In other embodiments, the anti-PD-L1 antibody is an antibody that binds to the same epitope as BMS-936559 or the anti-PD-L1 antibody disclosed in U.S. Pat. No. 7,943,743.

In other embodiments, the anti-PD-L1 antibody is MPDL3280A (also known as RG7446) (see, e.g., Herbst; U.S. Pat. No. 8,217,149), MEDI4736 (also called Durvalumab; Khleif, 2013, See U.S. Pat. No. 8,779,108 or US 2014/0356353, filed May 6, 2014), or MSB0010718C (also called Avelumab; See US 2014/0341917). In some embodiments, the anti-PD-L1 antibody is an antibody that cross-competes with MPDL3280A, MEDI4736, and/or MSB0010718C for binding. In other embodiments, the anti-PD-L1 antibody is an antibody that binds to the same epitope as MPDL3280A, MEDI4736, and/or MSB0010718C.

In certain embodiments, the antibodies that cross-compete for binding to human PD-L1 with, or bind to the same epitope region of human PD-L1 as the above-references PD-L1 antibodies, are monoclonal antibodies. For administration to human subjects, these cross-competing antibodies can be chimeric antibodies, or can be humanized or human antibodies. Such chimeric, humanized, or human monoclonal antibodies can be prepared and isolated by methods well known in the art.

Anti-PD-L1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody, or any combination thereof.

Anti-CTLA-4 Antibodies

Anti-CTLA-4 antibodies useful for the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing, or prolonging an immune response.

Human monoclonal antibodies that bind specifically to CTLA-4 with high affinity have been disclosed in U.S. Pat. Nos. 6,984,720 and 7,605,238. Other anti-CTLA-4 monoclonal antibodies have been described in, for example, U.S. Pat. Nos. 5,977,318, 6,051,227, 6,682,736, and 7,034,121. The anti-CTLA-4 human monoclonal antibodies disclosed in U.S. Pat. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ M$^{-1}$, about $10^9$ M$^{-1}$, or about $10^{10}$ M$^{-1}$ to $10^{11}$ M$^{-1}$ or higher, as determined by Biacore analysis; (b) a kinetic association constant ($k_a$) of at least about $10^3$, about $10^4$, or about $10^5$ m$^{-1}$ s$^{-1}$; (c) a kinetic disassociation constant ($k_d$) of at least about $10^3$, about $10^4$, or about $10^5$ m$^{-1}$ s$^{-1}$; and (d) inhibits the binding of CTLA-4 to B7-1 (CD80) and B7-2 (CD86). Anti-CTLA-4 antibodies usable in the present invention include monoclonal antibodies that bind specifically to human CTLA-4 and exhibit at least one, at least two, or at least three of the preceding characteristics.

An exemplary clinical anti-CTLA-4 antibody is the human monoclonal antibody 10D1 (now known as ipilimumab and marketed as YERVOY®) as disclosed in U.S. Pat. No. 6,984,720. Ipilimumab is an anti-CTLA-4 antibody for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

Another anti-CTLA-4 antibody usable in the present methods is tremelimumab (also known as CP-675,206). Tremelimumab is human IgG2 monoclonal anti-CTLA-4 antibody. Tremelimumab is described in WO2012/122444, U.S. Publ. No. 2012/263677, and WO 2007/113648 A2.

Anti-CTLA-4 antibodies usable in the disclosed methods also include isolated antibodies that bind specifically to human CTLA-4 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with ipilimumab or tremelimumab, or bind to the same epitope region of human CTLA-4 as does ipilimumab or tremelimumab, are antibodies comprising a heavy chain of the human IgG1 isotype. For administration to human subjects, these cross-competing antibodies can be chimeric antibodies, or can be humanized or human antibodies. Usable anti-CTLA-4 antibodies also include antigen-binding portions of the above antibodies such as Fab, F(ab')$_2$, Fd, or Fv fragments.

In some embodiments, an anti-PD-1 antibody is used in combination with an anti-CTLA-4 antibody in any method of the present invention.

Cancer and Standard-of-Care Therapies

In some embodiments, a standard of care therapy is used in any of the methods disclosed herein. In some embodiments, the therapeutic efficacy of any therapy disclosed herein is compared to a standard of care therapy. In certain embodiments, a standard of care therapy is used in combination with any other therapy disclosed herein. In some embodiments, a PD-1 antibody is used in combination with a standard-care-therapy in any method of the present invention. Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES®, 2014), available at: www.nccn.org/professionals/physician_gls/f_guidelines.asp, last accessed May 14, 2014).

Lung Cancer

In some embodiments, methods disclosed herein are directed to a cancer that is lung cancer. In certain embodiments, the cancer is NSCLC. In some embodiments, the NSCLC has a squamous histology. In other embodiments, the NSCLC has a non-squamous histology.

NSCLC is the leading cause of cancer death in the U.S. and worldwide, exceeding breast, colon and prostate cancer combined. In the U.S., an estimated 228,190 new cases of lung and bronchial will be diagnosed in the U.S., and some 159,480 deaths will occur because of the disease (Siegel et al. (2014) *CA Cancer J Clin* 64(1):9-29). The majority of patients (approximately 78%) are diagnosed with advanced/recurrent or metastatic disease. Metastases to the adrenal gland from lung cancer are a common occurrence, with about 33% of patients having such metastases. NSCLC therapies have incrementally improved OS, but benefit has reached a plateau (median OS for late stage patients is just 1 year). Progression after 1 L therapy occurred in nearly all of these subjects and the 5-year survival rate is only 3.6% in the refractory setting. From 2005 to 2009, the overall 5-year relative survival rate for lung cancer in the U.S. was 15.9% (NCCN GUIDELINES®, Version 3.2014—Non-Small Cell Lung Cancer, available at: www.nccn.org/professionals/physician_gls/pdf/nscl.pdf, last accessed May 14, 2014).

There are seven stages of NSCLC: Occult non-small cell lung cancer, Stage 0 (carcinoma in situ), Stage I, Stage II, Stage IIIA, Stage IIIB, and Stage IV.

In addition, the present methods can also be combined with surgery, radiation therapy (RT), and chemotherapy that are the three modalities commonly used to treat NSCLC patients. As a class, NSCLCs are relatively insensitive to chemotherapy and RT, compared to small cell carcinoma. In general, for patients with Stage I or II disease, surgical resection provides the best chance for cure, with chemotherapy increasingly being used both pre-operatively and post-operatively. RT can also be used as adjuvant therapy for patients with resectable NSCLC, the primary local treatment, or as palliative therapy for patients with incurable NSCLC.

In one embodiment, the subject suitable for the methods of the present invention is a patient with Stage IV disease. Patients with Stage IV disease have a good performance status (PS) benefit from chemotherapy. Many drugs, including platinum agents (e.g., cisplatin, carboplatin), taxanes agents (e.g., paclitaxel, albumin-bound paclitaxel, docetaxel), vinorelbine, vinblastine, etoposide, pemetrexed and gemcitabine are useful for Stage IV NSCLC. Combinations using many of these drugs produce 1-year survival rates of 30% to 40% and are superior to single agents. Specific targeted therapies have also been developed for the treatment of advanced lung cancer. For example, bevacizumab (AVASTIN®) is a monoclonal antibody that blocks vascular endothelial growth factor A (VEGF-A). Erlotinib (TARCEVA®) is a small-molecule TKI of epidermal growth factor receptor (EGFR). Crizotinib (XALKORI®) is a small-molecule TKI that targets ALK and MET, and is used to treat NSCLC in patients carrying the mutated ALK fusion gene. Cetuximab (ERBITUX®) is a monoclonal antibody that targets EGFR.

In some embodiments, the present methods are used to treat a subject who has squamous NSCLC. There is a particular unmet need among patients who have squamous cell NSCLC (representing up to 25% of all NSCLC) as there are few treatment options after first line (1L) therapy. Single-agent chemotherapy is standard of care following progression with platinum-based doublet (Pt-doublet) chemotherapy, resulting in median OS of approximately 7 months. Docetaxel remains the benchmark treatment in this line of therapy, although erlotinib can also be used with less frequency. Pemetrexed has also been shown to produce clinically equivalent efficacy outcomes, but with significantly fewer side effects compared with docetaxel in the second line (2L) treatment of patients with advanced NSCLC (Hanna et al., 2004 *J Clin Oncol* 22:1589-97). No therapy is currently approved for use in lung cancer beyond the third line (3L) setting. Pemetrexed and bevacizumab are not approved in squamous NSCLC, and molecularly targeted therapies have limited application. The unmet need in advanced lung cancer has been compounded by the recent failure of Oncothyreon and Merck KgaA's STIMUVAX® to improve OS in a phase 3 trial; inability of ArQule's and Daiichi Sankyo's c-Met kinase inhibitor, tivantinib, to meet survival endpoints; failure of Eli Lilly's ALIMTA® in combination with Roche's AVASTIN® to improve OS in a late-stage study; and Amgen's and Takeda Pharmaceutical's failure to meet clinical endpoints with the small-molecule VEGF-R antagonist, motesanib, in late-stage trials.

Colorectal Cancer

In some embodiments, methods disclosed herein are directed to a cancer that is colorectal cancer. In certain embodiments, the colorectal cancer is colon cancer. In other embodiments, the colorectal cancer is rectal cancer. In certain embodiments, the colorectal cancer has microsatellite instability (MSI). (See Pawlik et al., Dis. Markers 20(4-5): 199-206 (2004)). In other embodiments, the colorectal cancer has low microsatellite instability (MSI-L).

Colorectal cancer is the third most common type of cancer in both men and women in the U.S. (See http://www.cancer.gov/types/colorectal, last visited Dec. 9, 2015). Most colorectal cancers are adenocarcinomas. Colon cancer presents in five stages: Stage 0 (Carcinoma in Situ), Stage I, Stage II, Stage III, and Stage IV. Six types of standard treatment are used for colon cancer: 1) surgery, including a local excision, resection of the colon with anastomosis, or resection of the colon with colostomy; 2) radiofrequency ablation; 3) cryosurgery; 4) chemotherapy; 5) radiation therapy; and 6) targeted therapies, including monoclonal antibodies and angiogenesis inhibitors.

Rectal cancer presents in five stages: Stage 0 (Carcinoma in Situ), Stage I, Stage II, Stage III, and Stage IV. Six types of standard treatment are used for rectal cancer: 1) surgery, including polypectomy, local excision, resection, radiofrequency ablation, cryosurgery, and pelvic exenteration; 2) radiation therapy; 3) chemotherapy; and 4) targeted therapy, including monoclonal antibody therapy. In some embodiments, the methods of the invention treat a rectal cancer.

Melanoma

In some embodiments, methods disclosed herein are directed to a cancer that is melanoma. Melanoma is the most deadly form of skin cancer, and is the fifth most common cancer diagnosis in men and the seventh most common cancer diagnosis in women. (See http://www.cancer.gov/types/skin, last visited Dec. 9, 2015). Melanoma presents in seven stages: Stage 0 (Melanoma in situ), Stage I, Stage II, Stage III that can be removed by surgery, Stage III that cannot be removed by surgery, Stage IV, and Recurrent Melanoma. Five standard types of treatment are used: 1) surgery; 2) chemotherapy; 3) radiation therapy and 4) biologic therapy, including interferon, interleukin-2 (IL-2), tumor necrosis factor (TNF) therapy, and Ipilimumab; and 5) targeted therapy, including signal transduction inhibitor therapy (e.g., vemurafenib, dabrafenib, and trametinib), oncolytic virus therapy, monoclonal antibody therapy (including pembrolizumab and nivolumab), and angiogenesis inhibitors.

Ovarian Cancer

In some embodiments, methods disclosed herein are directed to a cancer which is ovarian, fallopian tube, and primary peritoneal cancer ("ovarian cancer"). In certain embodiments, the cancer is ovarian epithelial cancer. In other embodiments, the cancer is ovarian germ cell tumor. In yet other embodiments, the cancer is an ovarian low malignant potential tumor. In further embodiments, the ovarian cancer begins in the tissue that covers the ovaries, the peritoneum or the fallopian tube. (See http://www.cancer-.gov/types/ovarian/patient/ovarian-epithelial-treatment-pdq, last visited Dec. 9, 2015).

There are four stages of ovarian cancer: Stage I, Stage II, Stage III, and Stage IV, which encompass early, advanced and recurrent or persistent ovarian cancer. There are four types of standard treatments that are used for patients with ovarian, fallopian tube, and primary peritoneal cancer: 1) surgery, including hysterectomy, unilateral salpingo-oophorectomy, bilateral salpingo-oophorectomy, omentectomy, and lymph node biopsy; 2) radiation therapy; 3) chemotherapy; and 4) targeted therapy, including monoclonal antibody therapy and poly (ADP-ribose) polymerase inhibitors. Biologic therapies are also being tested for ovarian cancer.

There are four stages of ovarian germ cell tumors: Stage I, Stage II, Stage III and Stage IV. Four types of standard treatment are used: 1) surgery, including unilateral salpingo-oophorectomy, total hysterectomy, bilateral salpingo-oophorectomy, and tumor debulking; 2) observation; 3) chemotherapy; and 4) radiation therapy. New treatment options being considered include high-dose chemotherapy with bone marrow transplant.

There are 3 stages of ovarian low malignant potential tumors: 1) early stage (Stage I and II); 2) late stage (Stage III and IB); and 3) recurrent. Two types of standard treatment are used: 1) surgery, including unilateral salpingo-oophorectomy, bilateral salpingo-oophorectomy, total hysterectomy, partial oophorectomy, and omentectomy; and 2) chemotherapy.

Head and Neck Cancer

In some embodiments, methods disclosed herein are directed to a cancer that is head and neck cancer. Head and neck cancers include cancers of the oral cavity, pharynx, larynx, paranasal sinuses, nasal cavity, and salivary glands. Head and neck cancers usually begin in the squamous cells that line the moist, mucosal surfaces inside the head and neck (for example, inside the mouth, the nose, and the throat). These squamous call cancers are often referred to as squamous cell carcinomas of the head and neck. Head and neck cancers can also begin in the salivary glands, but salivary gland cancers are relatively uncommon. (See http://www.cancer.gov/types/head-and-neck/head-neck-fact-sheet, last visited Dec. 9, 2015). The treatment plan for an individual patient depends on a number of factors, including the exact location of the tumor, the stage of the cancer, and the person's age and general health. Treatment for head and neck cancer can include surgery, radiation therapy, chemotherapy, targeted therapy, or a combination of treatments.

Pharmaceutical Compositions and Dosages

Therapeutic agents of the present invention can be constituted in a composition, e.g., a pharmaceutical composition containing an antibody and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In some embodiments, the carrier for a composition containing an antibody is suitable for intravenous, intramuscular, subcutaneous, parenteral, spinal or epidermal administration (e.g., by injection or infusion). A pharmaceutical composition of the invention can include one or more pharmaceutically acceptable salts, anti-oxidant, aqueous and non-aqueous carriers, and/or adjuvants such as preservatives, wetting agents, emulsifying agents and dispersing agents.

Dosage regimens are adjusted to provide the optimum desired response, e.g., a maximal therapeutic response and/or minimal adverse effects. In some embodiments, for example, the anti-PD-1 antibody is administered at a weight-based dose. For administration of an anti-PD-1 antibody, the dosage can range from at least about 0.01 to at least about 20 mg/kg, from at least about 0.1 to at least about 10 mg/kg, from about 0.01 to about 5 mg/kg, from about 1 to about 5 mg/kg, from about 2 to about 5 mg/kg, from about 1 to about 3 mg/kg, from about 7.5 to about 12.5 mg/kg, or from about 0.1 to about 30 mg/kg of the subject's body weight. For example, dosages can be at least about 0.1 mg/kg, at least about 0.3 mg/kg, at least about 1 mg/kg, at least about 2 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, or at least about 10 mg/kg body weight, and at least about 0.3 mg/kg, at least about 1 mg/kg, at least about 2 mg/kg, at least about 3 mg/kg, or at least about 5 mg/kg body weight. In certain embodiments, the dosage of the anti-PD-1 antibody is 3 mg/kg body weight.

In one embodiment, a dosage regimen for an anti-PD-1 antibody of the invention comprises about 0.3 mg/kg to 1 mg/kg body weight, about 5 mg/kg body weight, 1 mg/kg to 5 mg/kg body weight, or about 1 mg/kg to about 3 mg/kg body weight via intravenous administration, with the antibody being given every about 14-21 days in up to about 6-week or about 12-week cycles until complete response or confirmed progressive disease. In some embodiments, the antibody treatment, or any combination treatment disclosed herein, is continued for at least about 1 month, at least about 2 months, at least about 3 months, at least about 4 months, at least about 5 months, at least about 6 months, at least about 9 months, at least about 1 year, at least about 18 months, at least about 24 months, at least about 3 years, at least about 5 years, or at least about 10 years.

In certain embodiments, the dose of an anti-PD-1 antibody is a fixed dose in a pharmaceutical composition. In other embodiments, the method of the present invention can be used with a flat dose (a dose given to a patient irrespective of the body weight of the patient). In some embodiments, the flat dose of the anti-PD-1 antibody is at least about 100 mg, 120 mg, 140 mg, 160 mg, 180 mg, 200 mg, 220 mg, 240 mg, 260 mg, 280 mg, 300 mg, 360 mg, 400 mg, 420 mg, 440 mg, 460 mg, 480 mg, 500 mg, 520 mg, 540 mg, 560 mg or 600 mg; at least about 100-500 mg, such as, at least about 200-300 mg, at least about 220-260 mg, at least about 230-250 mg, at least about 300-500 mg, or at least about 400-500 mg or at least about 240 mg, such as at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, or at least about 500 mg. In some embodiments, the anti-PD-1 antibody is administered at a flat dose of 360 mg once about every three weeks. In other embodiments, the anti-PD-1 antibody is administered at a flat dose of 480 mg once about every four weeks.

In some embodiments, the anti-PD-1 antibody is administered in a fixed dose with a second therapy. In certain embodiments, the second therapy is an antibody. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg anti-PD-1 antibody to mg second antibody.

The dosing schedule is typically designed to achieve exposures that result in sustained receptor occupancy (RO) based on typical pharmacokinetic properties of an antibody. An exemplary treatment regime entails administration once per week, once about every 2 weeks, once about every 3 weeks, once about every 4 weeks, once about a month, once about every 3-6 months or longer. In certain embodiments, an anti-PD-1 antibody such as nivolumab is administered to the subject once about every 2 weeks. In other embodiments, the antibody is administered once about every 3 weeks. In further embodiments, the antibody is administered once about every 4 weeks. The anti-PD-1 antibody can be administered in at least two doses, each of the doses is at an amount of about 0.01 mg/kg to about 5 mg/kg, e.g., 3 mg/kg, at a dosing interval of every two weeks between the two doses. In some embodiments, the anti-PD-1 antibody is administered in at least three, four, five, six, or seven doses (i.e., multiple doses), each of the doses is at an amount of about 0.01 mg/kg to about 5 mg/kg, e.g., 3 mg/kg, at a dosing interval of every two weeks between two adjacently given doses. The dosage and scheduling can change during a course of treatment.

When used in combinations with other anti-cancer agents, the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%). (Brahmer et al. (2010) *J Clin Oncol* 28:3167-75). In some embodiments, 0.3 mg/kg dosing can allow for sufficient exposure to lead to maximal biologic activity.

Treatment is continued as long as clinical benefit is observed or until unacceptable toxicity or disease progression occurs. In certain embodiments, the anti-PD-1 antibody can be administered at the dosage that has been shown to produce the highest efficacy as monotherapy in clinical trials, e.g., about 3 mg/kg of nivolumab administered once about every three weeks (Topalian et al., 2012 *N Engl J Med* 366:2443-54; Topalian et al., 2012 *Curr Opin Immunol* 24:207-12), or at a significantly lower dose, i.e., at a subtherapeutic dose.

Dosage and frequency vary depending on the half-life of the antibody in the subject. In general, human antibodies show the longest half-life, followed by humanized antibodies, chimeric antibodies, and non-human antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, and until the patient shows partial or complete amelioration of symptoms of disease. Thereafter, the patient can be administered a prophylactic regime.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Kits

Also within the scope of the present invention are kits comprising an anti-PD-1 antibody and, optionally, another anti-cancer agent for therapeutic uses. Kits typically include a label indicating the intended use of the contents of the kit and instructions for use. The term "label" includes any writing or recorded material supplied on or with the kit, or which otherwise accompanies the kit. Accordingly, this disclosure provides a kit for treating a subject afflicted with a cancer, the kit comprising: (a) a dosage of an anti-PD-1 antibody or antigen-binding portion thereof; optionally, (b) a dosage of a second anti-cancer agent; and (c) instructions for using the anti-PD-1 antibody and, optionally, the second anti-cancer agent in any of the therapy methods disclosed herein. In certain embodiments for treating human patients, the kit comprises an anti-human PD-1 antibody disclosed herein, e.g., nivolumab, pembrolizumab, MEDI0680 (formerly AMP-514), AMP-224, or BGB-A317. In some embodiments, the kit comprises an anti-human PD-L1 antibody disclosed herein, e.g., BMS-936559, MPDL3280A, MEDI4736, and/or MSB0010718C The present invention is further illustrated by the following examples, which should not be construed as further limiting. The contents of all references cited throughout this application are expressly incorporated herein by reference.

Cross-Reference to Earlier Filed Applications: this application claims benefit to U.S. Provisional Application No. 62/318,701, filed Apr. 5, 2016, which is incorporated herein by reference in its entirety.

EXAMPLES

Example 1

Clinical Case Study of the Association Between Cytokine Score (Cytoscore) and Overall Survival (OS) in Advanced Refractory Squamous Cell Non-Small Cell Lung Cancer Patients Treated with Nivolumab or Docetaxel Baseline serum cytokine concentrations were collected prior to therapy from evaluable patients with squamous (SQ) non-small cell lung cancer (NSCLC) treated with nivolumab (n=222) or docetaxel (n=118) in clinical studies.

A three-step approach was used in the analysis. A schematic of the analysis is shown in FIG. 1, and a model evaluation of selected cytokines is shown in FIGS. 2A-2F.

Figure 3:
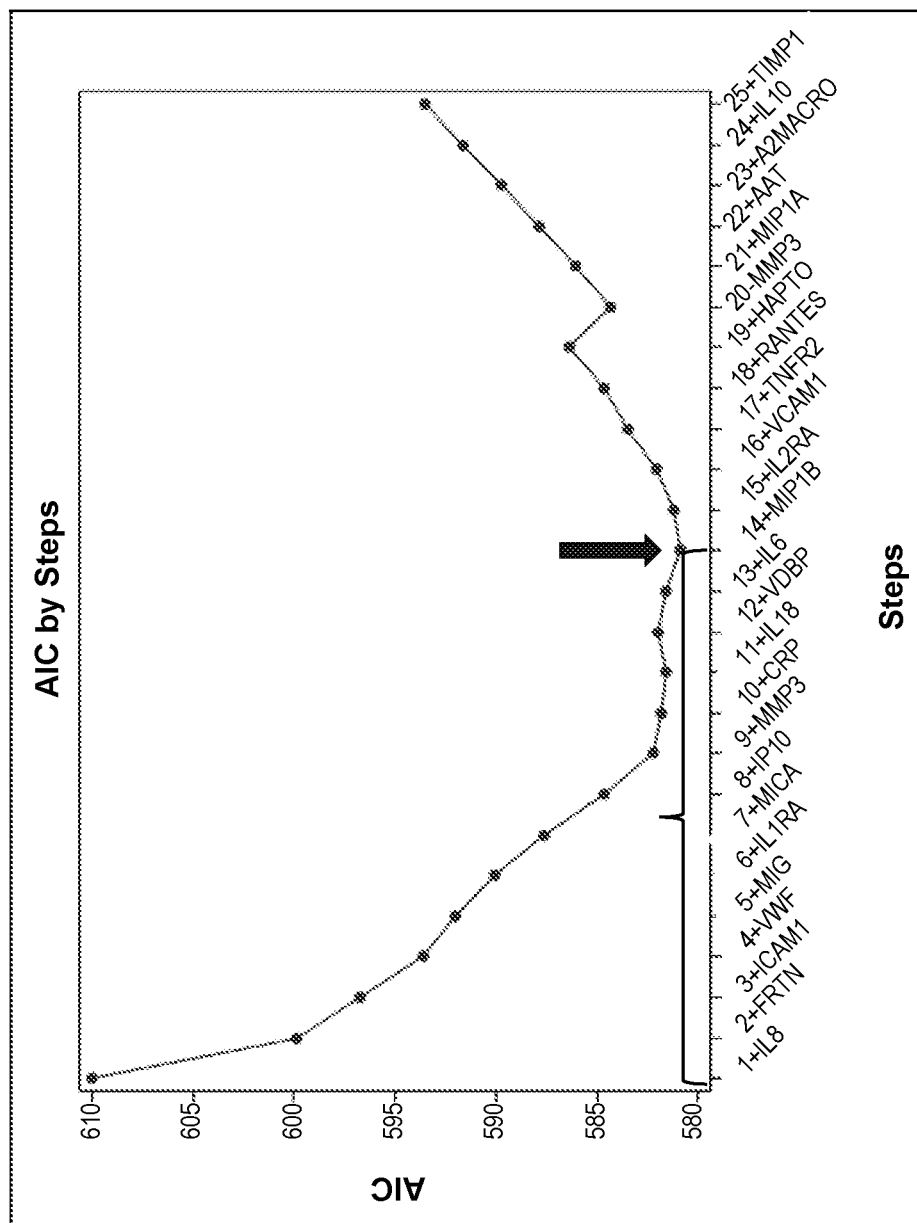
FIG. 3 shows the calculation of cytokines associated with overall survival (OS) in nivolumab-treated squamous cell non-small cell lung cancer patients via stepwise variable selection in a Cox model. AIC, Akaike information criterion.

Patients were divided into a training set (60% of patients) and a validation set (40% of patients). Twenty-eight serum cytokine concentrations at baseline were evaluated using a custom HumanMAP quantitative multiplexed immunoassay (Myriad RBM, Austin, Tex.) (forty-nine cytokines were tested, but only twenty-eight were detectable). To identify a set of serum cytokines that at baseline may be associated with overall survival (OS) in patients treated with nivolumab, a stepwise variable selection in a Cox model was performed on 60% randomly split cytokine data from the two nivolumab clinical studies. FIG. 3 shows the stepwise variable selection methodology used to identify cytokines associated with overall survival.

The predictive performance of the cytokine model was tested using time-varying receiver-operating characteristic (ROC) analysis in the training (60%) set and then validated in the validation (40%) test set. FIGS. 4A-4J show the ROC analysis used to test the association of the identified cytokine set with OS.

Figure 5B:
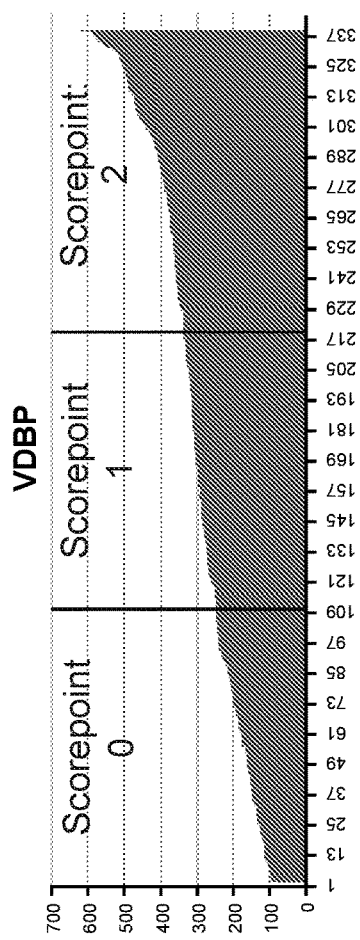
FIGS. 5A-5C show the method of calculating the cytokine score for patients with advanced or metastatic squamous cell non-small cell lung cancer (SQ-Cytoscore) (FIG. 5A), and representative tertile bin distributions for select cytokines associated positively with overall survival (OS) (FIG. 5B) or negatively associated with overall survival (OS) (FIG. 5C).
Figure 5C:
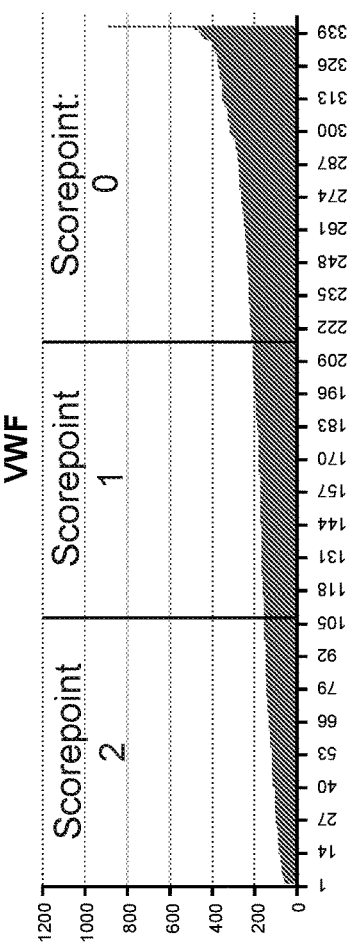
Figure 5A:
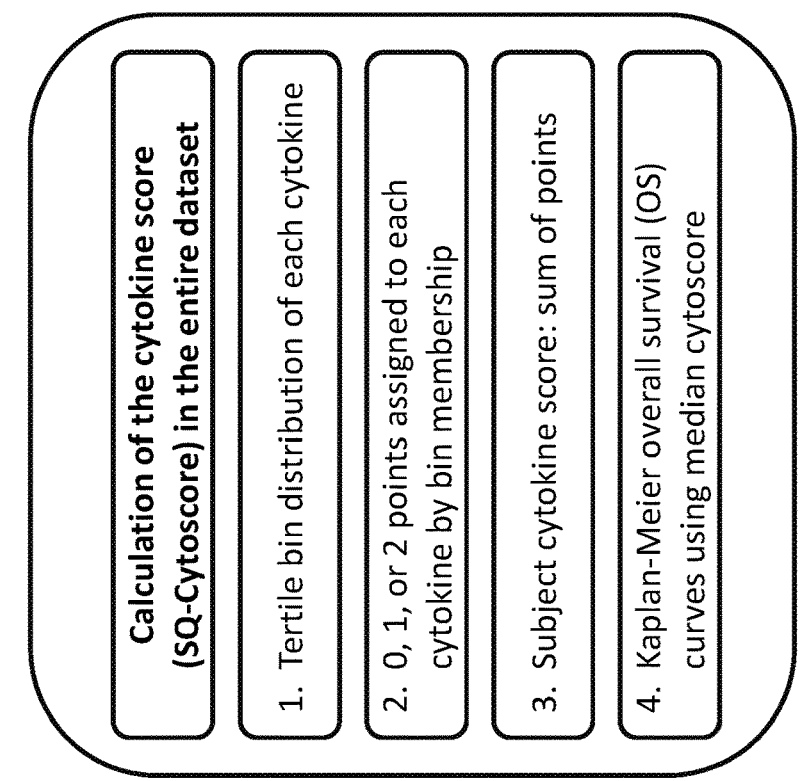

To quantify the benefit of the cytokine set to OS, a squamous-cytokine score (SQ-Cytoscore) was computed as follows: i) calculation of the tertile bin distribution of each cytokine in all patients and assignment of a point score (0, 1, or 2 for cytokines positively associated with OS, and 2, 1, or 0 for cytokines negatively associated with OS) to each patient based on the bin membership; ii) calculation of the cytoscore for each subject as the sum of cytokine points; and iii) categorization of subjects as SQ-Cytoscore "high" or "low" based on the median SQ-Cytoscore cutoff. FIGS. 5A-5C show the methodology for calculating the SQ-Cytoscore and provides representative tertile bin distributions for select cytokines associated positively or negatively with OS. Kaplan-Meier curves were plotted for SQ-Cytoscore strata to compare OS in patients with high versus low SQ-Cytoscore in each arm. Interactions between SQ-Cytoscore levels and: i) treatment; ii) Eastern Cooperative Oncology Group (ECOG) score; and iii) PD-L1 status were then investigated using significance tests for Chi-square statistic.

A set of 14 cytokines was found to be strongly associated with OS in the training set. A time-varying ROC analysis showed a good model performance from 6 to 18 months in the training and validation sets (based on 18-month OS data from June 2015 database lock and August 2015 database lock).

Figure 6A:
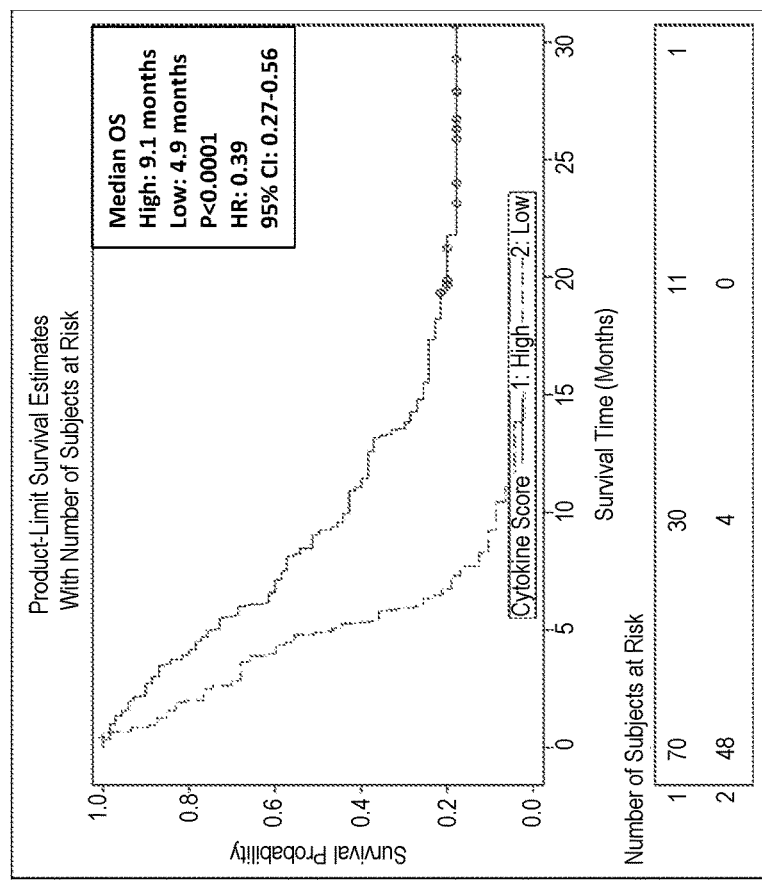
FIGS. 6A-6B show the overall survival (OS) of nivolumab-treated squamous cell non-small cell lung cancer patients with a high cytoscore or a low cytoscore (FIG. 6A) compared to the OS of docetaxel-treated squamous cell non-small cell lung cancer patients with high cytoscore or low cytoscore (FIG. 6B).
Figure 6B:
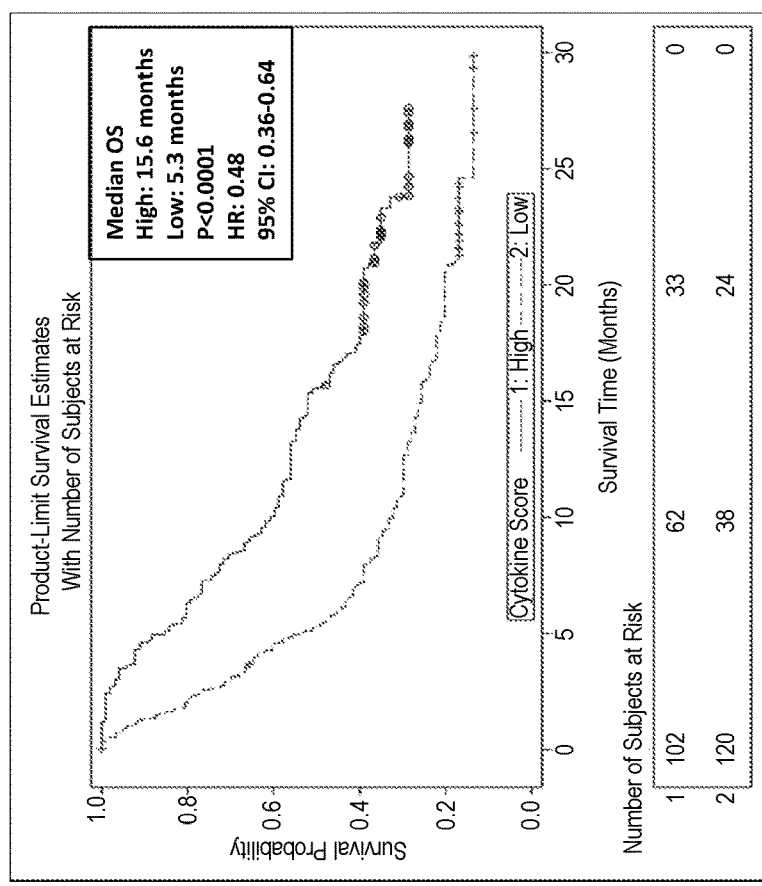

In patients treated with nivolumab, the median OS was 15.6 months in patients with a high SQ-Cytoscore versus 5.3 months in patients with a low SQ-Cytoscore (HR: 0.48, 95% CI: 0.36-0.64, p<0.0001). Therefore, an increase in OS of 10.3 months was observed in high SQ-Cytoscore patients treated with nivolumab. In patients treated with docetaxel, the median OS was 9.1 months in patients with a high SQ-Cytoscore versus 4.9 months in patients with a low SQ-Cytoscore (HR: 0.39, 95% CI: 0.27-0.56, p<0.0001). Therefore, an increase in OS of 4.2 months was observed in high SQ-Cytoscore patients treated with docetaxel. FIGS. 6A-6B show the Kaplan-Meier survival curves for high cytoscore and low cytoscore patients treated with nivolumab compared to the Kaplan-Meier survival curves for high cytoscore and low cytoscore patients treated with docetaxel.

Figure 7A:
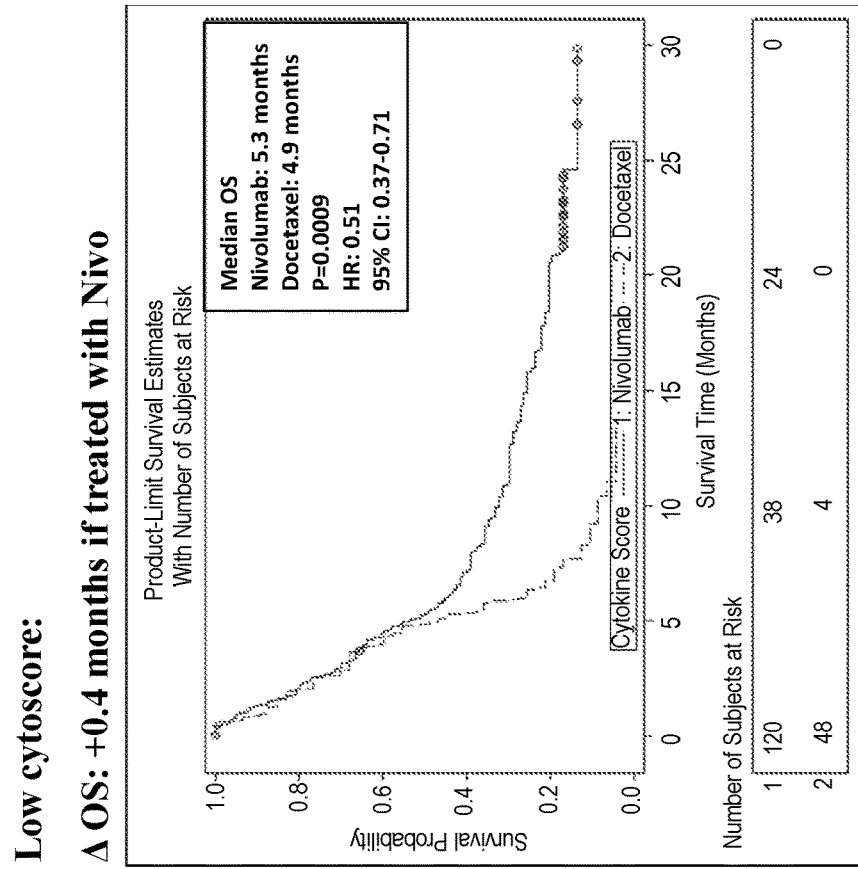
FIGS. 7A-7B shows the overall survival (OS) of high cytoscore squamous cell non-small cell lung cancer patients treated with nivolumab or docetaxel (FIG. 7A) compared to the OS of low cytoscore squamous cell non-small cell lung cancer patients treated with nivolumab or docetaxel (FIG. 7B).
Figure 7B:
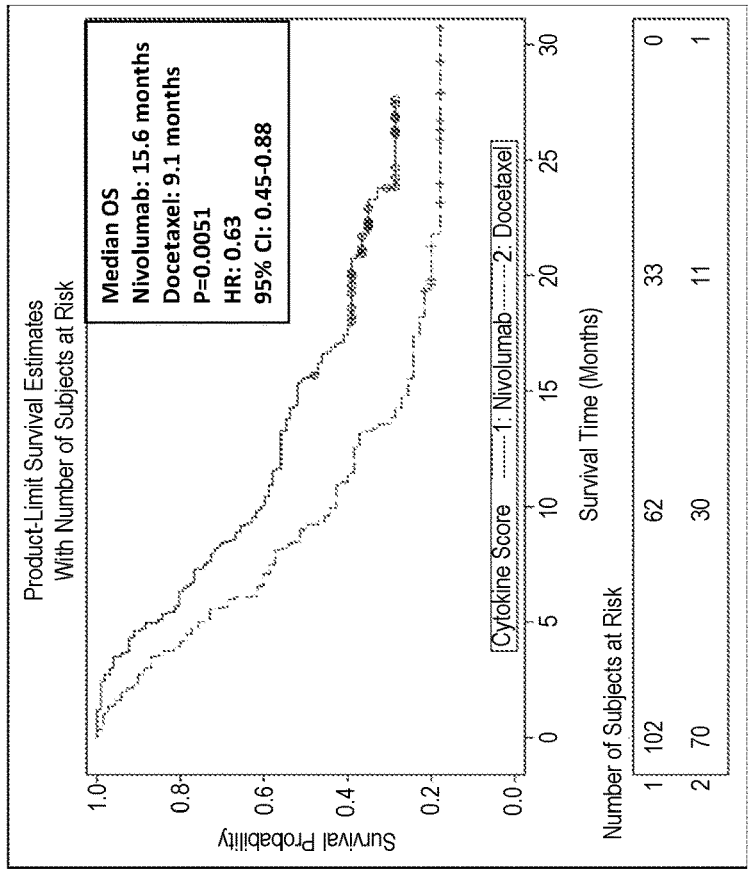

Among patients with high SQ-Cytoscores (n=172), median OS was 15.6 months for patients treated with nivolumab versus 9.1 months for patients treated with docetaxel (HR: 0.63, 95% CI: 0.45-0.88, p=0.0051). Among patients with low SQ-Cytoscores (n=168), median OS was 5.3 months for patients treated with nivolumab versus 4.9 months for patients treated with docetaxel (HR: 0.51, 95% CI: 0.37-0.71, P=0.0009). FIGS. 7A-7B show the Kaplan-Meier survival curves for high cytoscore patients treated with either nivolumab or docetaxel compared to low cytoscore patients treated with either nivolumab or docetaxel.

In nivolumab-treated patients, there was no interactive effective on OS between SQ-Cytoscore and treatment (p=0.37), ECOG status (p=0.72), or PD-L1 tumor positivity (p=0.68).

Example 2

Figure 8:
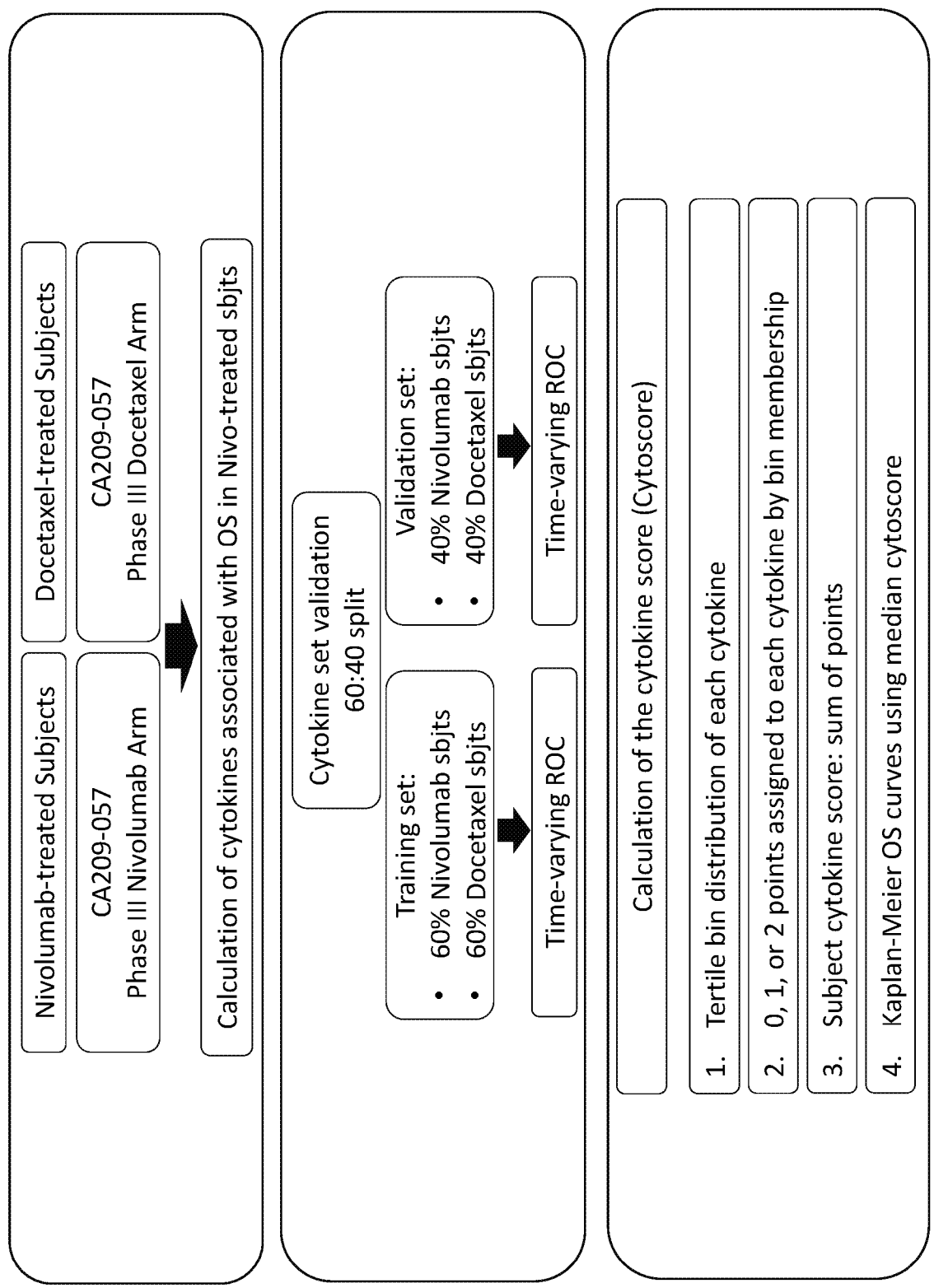
FIG. 8 shows a schematic of the method of determining cytokines associated with overall survival (OS) and calculating the cytoscore in patients with non-squamous cell non-small cell lung cancer. Sbjts, subjects; ROC, receiver-operating characteristic.

Clinical Case Study of the Association Between Cytokine Score (Cytoscore) and Overall Survival (OS) in Advanced Non-Squamous Non-Small Cell Lung Cancer Patients Treated with Nivolumab or Docetaxel Baseline serum cytokine concentrations were collected prior to therapy from evaluable patients with non-squamous (NSQ) non-small cell lung cancer (NSCLC) treated with nivolumab (n=240) or docetaxel (n=240) in the CheckMate 057 clinical study. A schematic of the analysis is shown in FIG. 8.

Figure 9:
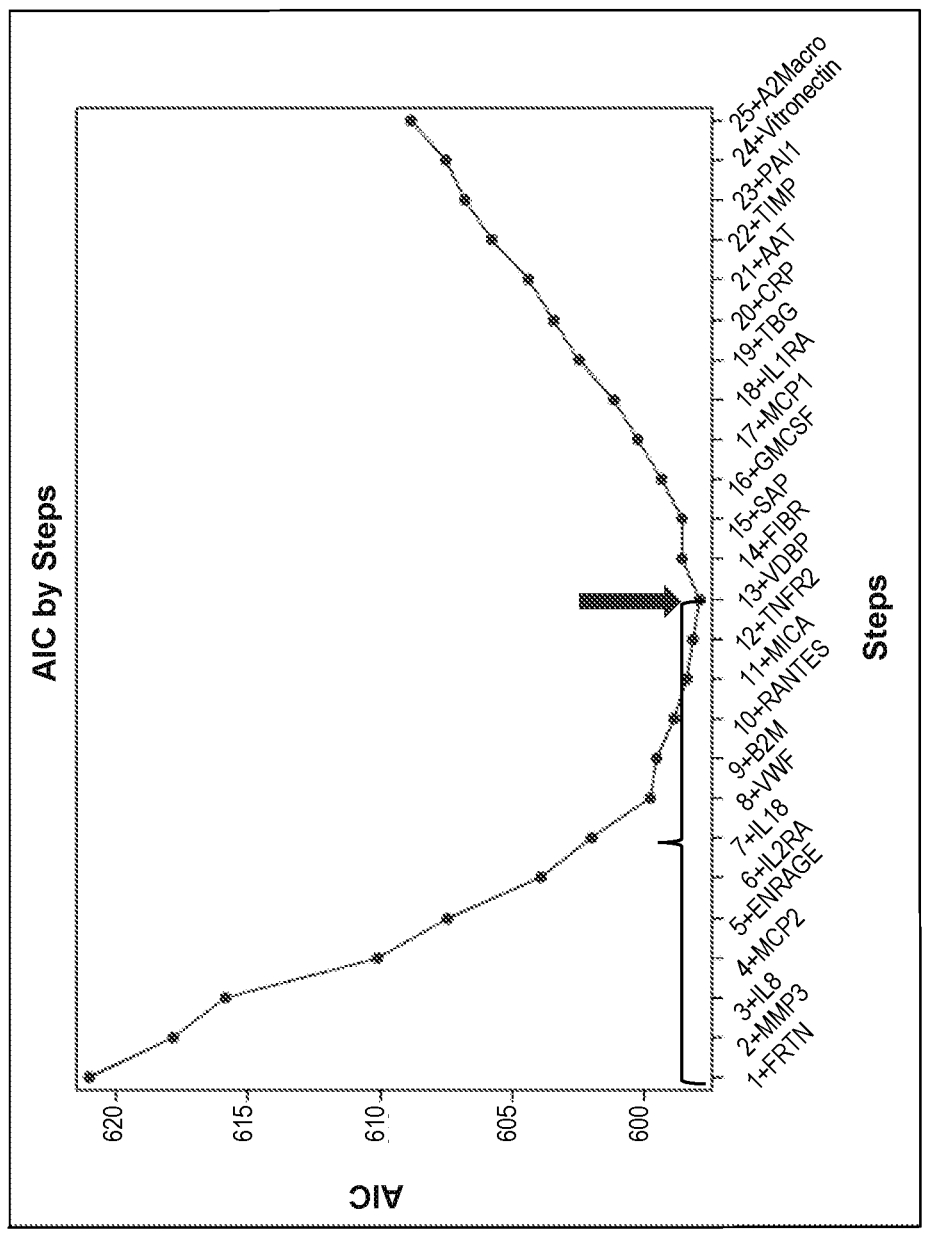
FIG. 9 shows the calculation of cytokines associated with overall survival (OS) in nivolumab-treated metastatic non-squamous non-small cell lung cancer patients via stepwise variable selection in a Cox model.

Patients were divided into a training set (60% of patients) and a validation set (40% of patients). Serum cytokine concentrations at baseline were evaluated using a custom HumanMAP quantitative multiplexed immunoassay (Myriad RBM, Austin, Tex.). To identify a set of serum cytokines that at baseline may be associated with overall survival (OS) in patients treated with nivolumab, a stepwise variable selection in a Cox model was performed on 60% randomly split cytokine data from the two nivolumab clinical studies. FIG. 9 shows the stepwise variable selection methodology used to identify cytokines associated with overall survival.

The predictive performance of the cytokine model was tested using time-varying receiver-operating characteristic (ROC) analysis in the training (60%) set and then validated in the validation (40%) test set. FIGS. 10A-10J show the ROC analysis used to test the association of the identified cytokine set with OS.

To quantify the benefit of the cytokine set to OS, a cytokine score (cytoscore) was computed as follows: i) calculation of the tertile bin distribution of each cytokine in all patients and assignment of a point score (0, 1, or 2 for cytokines positively associated with OS, and 2, 1, or 0 for cytokines negatively associated with OS) to each patient based on the bin membership; ii) calculation of the cytoscore for each subject as the sum of cytokine points; and iii) categorization of subjects as cytoscore "high" or "low" based on the median cytoscore cutoff. Kaplan-Meier curves were plotted for cytoscore strata to compare OS in patients with high versus low cytoscore in each arm. Interactions between cytoscore levels and: i) treatment; ii) Eastern Cooperative Oncology Group (ECOG) score; and iii) PD-L1 status were then investigated using significance tests for Chi-square statistic.

Figure 11A:
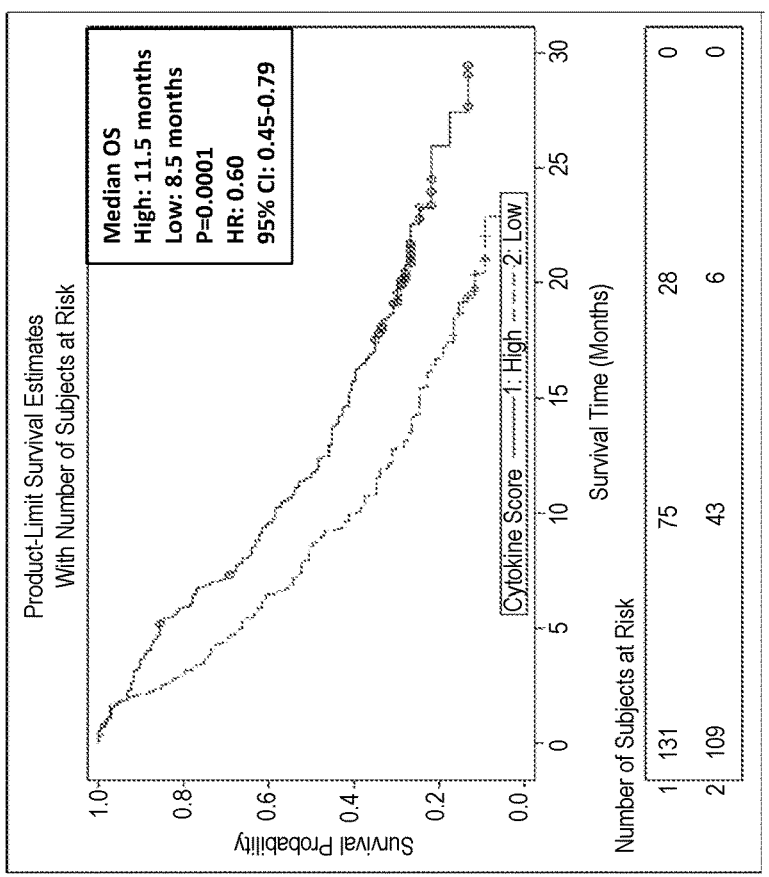
FIGS. 11A-11B show the overall survival (OS) of nivolumab-treated non-squamous non-small cell lung cancer patients with a high cytoscore or a low cytoscore (FIG. 11A) compared to the OS of docetaxel-treated non-squamous non-small cell lung cancer patients with a high cytoscore or a low cytoscore (FIG. 11B).
Figure 11B:
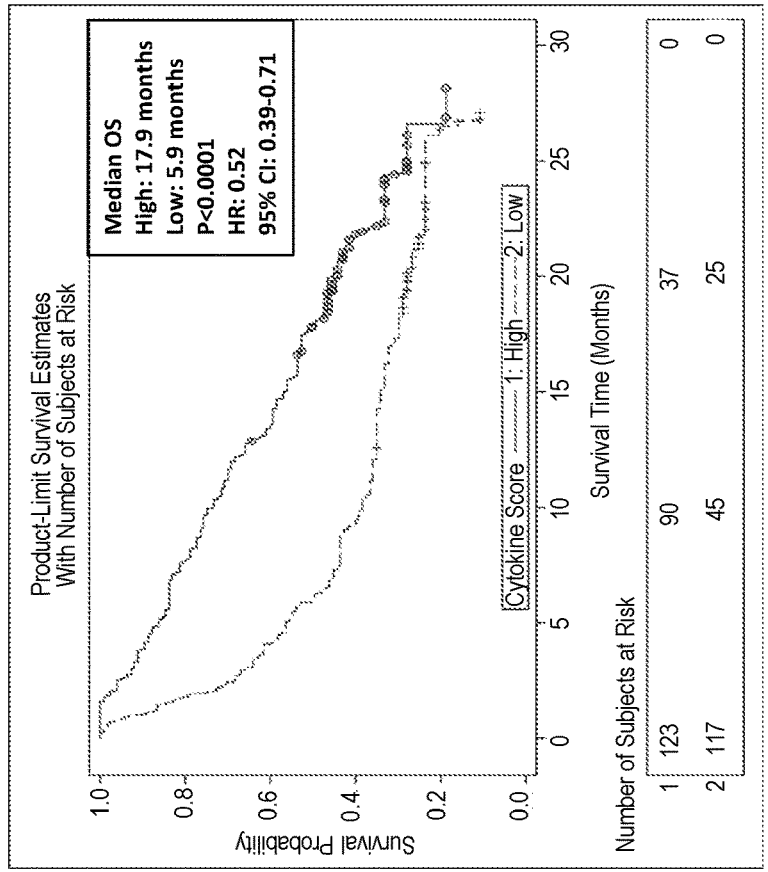

A set of 13 cytokines was found to be strongly associated with OS in the training set. A time-varying ROC analysis showed a good model performance from six to 18 months in the training and validation sets. In patients treated with nivolumab, the median OS was 17.9 months in patients with a high cytoscore versus 5.9 months in patients with a low cytoscore (HR: 0.52, 95% CI: 0.39-0.71, p<0.0001). Therefore, an increase in OS of 12 months was observed in high NSQ-Cytoscore patients treated with nivolumab. In patients treated with docetaxel, the median OS was 11.5 months in patients with a high cytoscore versus 8.5 months in patients with a low cytoscore (HR: 0.60, 95% CI: 0.45-0.79, p<0.0001). Therefore, an increase in OS of 3 months was observed in high NSQ-Cytoscore patients treated with docetaxel. FIGS. 11A-11B show the Kaplan-Meier survival curves for high cytoscore and low cytoscore patients treated with nivolumab compared to the Kaplan-Meier survival curves for high cytoscore and low cytoscore patients treated with docetaxel.

Figure 12A:
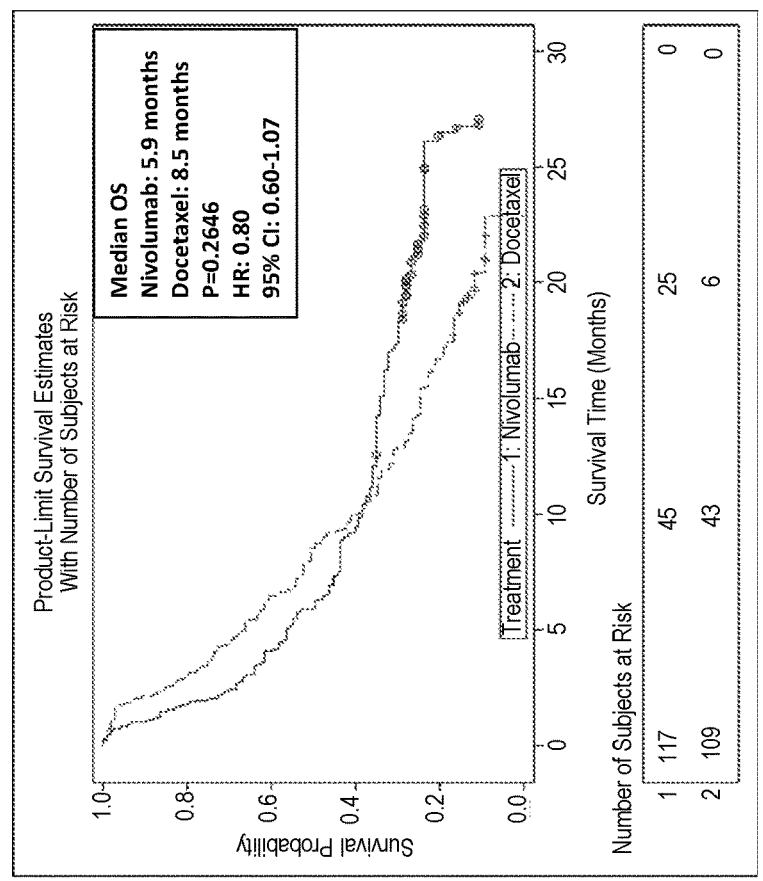
FIGS. 12A-12B show the overall survival (OS) of high cytoscore non-squamous non-small cell lung cancer patients treated with nivolumab or docetaxel (FIG. 12A) compared to the OS of low cytoscore non-squamous non-small cell lung cancer patients treated with nivolumab or docetaxel (FIG. 12B).
Figure 12B:
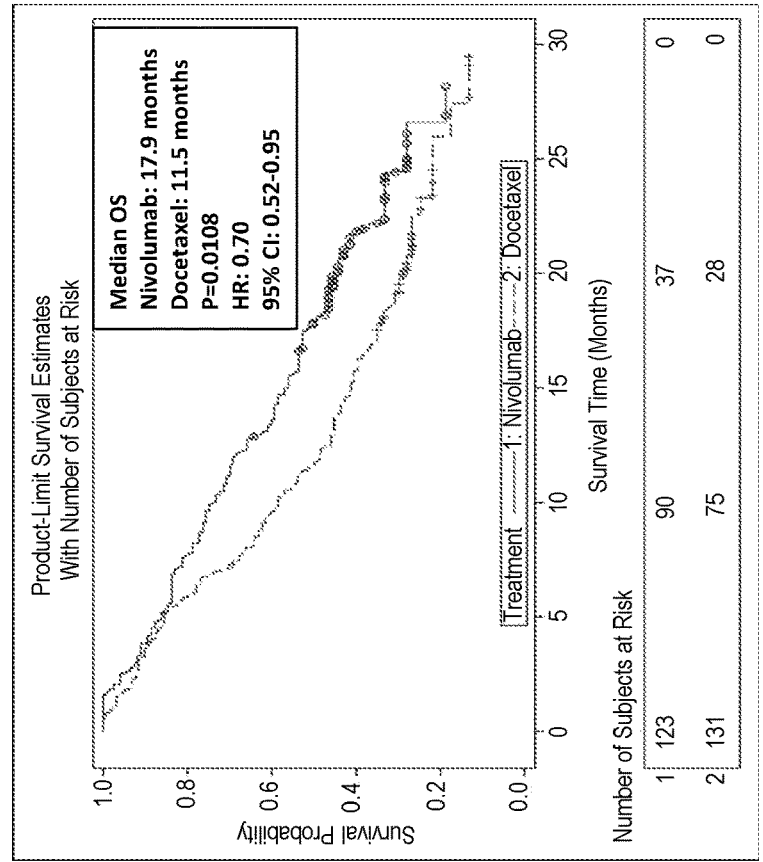

Among patients with high NSQ-Cytoscores (n=254), median OS was 17.9 months for patients treated with nivolumab versus 11.5 months for patients treated with docetaxel (HR: 0.70, 95% CI: 0.52-0.95, p=0.0108). Therefore, treatment with nivolumab provided an increase in OS of 6.4 months in high NSQ-Cytoscore patients. Among patients with low cytoscores (n=226), median OS was 5.9 months for patients treated with nivolumab versus 8.5 months for patients treated with docetaxel. Therefore, treatment with nivolumab did not provide a significant increase in OS in low NSQ-Cytoscore patients. FIGS. 12A-12B show the Kaplan-Meier survival curves for high NSQ-Cytoscore patients treated with either nivolumab or docetaxel compared to low NSQ-Cytoscore patients treated with either nivolumab or docetaxel.

What is claimed is:

1. A method of treating a human patient in need of an anti-cancer treatment comprising (i) determining a concentration level of one or more cytokines selected from the group consisting of MIG, IL-1RA, MMP-3, and any combination thereof and one or more cytokines selected from the group consisting of IL-8, FRTN, ICAM, VWF, MICA, IP-10, CRP, IL-18, IL-6, MIP1B, and any combination thereof; and (ii) administering to the patient an effective amount of an anti-PD-1 antibody or antigen-binding portion thereof ("anti-PD-1 antibody") or an effective amount of an anti-PD-L1 antibody or antigen-binding portion thereof ("anti-PD-L1 antibody").

2. The method of claim 1, wherein the patient has lung cancer.

3. The method of claim 2, wherein the lung cancer is non-small cell lung cancer.

4. The method of claim 1, wherein the patient has a high concentration level of at least two cytokines selected from the group consisting of MIG, IL-1RA, and MMP-3.

5. The method of claim 1, wherein the patient has a low concentration level of at least two cytokines selected from the group consisting of IL-8, FRTN, ICAM, VWF, MICA, IP-10, CRP, IL-18, IL-6, and MIP1B.

6. The method of claim 1, wherein the anti-PD-1 antibody is nivolumab.

7. The method of claim 1, wherein the anti-PD-L1 antibody is selected from BMS-936559, MPDL3280A, MEDI4736, and MSB0010718C.

8. The method of claim 1, wherein the anti-PD-1 antibody is pembrolizumab.

9. The method of claim 1, wherein the patient has a high concentration level of MIG, IL-1RA, and MMP-3.

10. The method of claim 1, wherein
   (i) a sample obtained from the patient has a high concentration level of the one or more cytokines selected from the group consisting of MIG, IL-1RA, MMP-3, and any combination thereof; and
   (ii) a sample obtained from the patient has a low concentration level of one or more cytokines selected from the group consisting of IL-8, FRTN, ICAM, VWF, MICA, IP-10, CRP, IL-18, IL-6, MIP1B, and any combination thereof;
   wherein the high concentration level and/or the low concentration level is determined by comparing the concentration level of the cytokine in the sample obtained from the patient to an average concentration level of the cytokine in a population of patients.

* * * * *